United States Patent
Rose et al.

(10) Patent No.: US 9,951,327 B1
(45) Date of Patent: Apr. 24, 2018

(54) EFFICIENT AND RAPID METHOD FOR ASSEMBLING AND CLONING DOUBLE-STRANDED DNA FRAGMENTS

(71) Applicant: Integrated DNA Technologies, Inc., Coralville, IA (US)

(72) Inventors: Scott D. Rose, Coralville, IA (US); Joseph A. Walder, Chicago, IL (US); Kristin Beltz, Cedar Rapids, IA (US); Shawn Allen, Williamsburg, IA (US)

(73) Assignee: INTEGRATED DNA TECHNOLOGIES, INC., Coralville, IA (US)

( * ) Notice: Subject to any disclaimer, the term of this patent is extended or adjusted under 35 U.S.C. 154(b) by 304 days.

(21) Appl. No.: 14/802,989

(22) Filed: Jul. 17, 2015

Related U.S. Application Data

(60) Provisional application No. 62/025,822, filed on Jul. 17, 2014.

(51) Int. Cl.
*C12N 9/00* (2006.01)
*C12N 9/16* (2006.01)
*C12N 9/12* (2006.01)

(52) U.S. Cl.
CPC .............. *C12N 9/93* (2013.01); *C12N 9/1252* (2013.01); *C12N 9/16* (2013.01); *C12Y 207/07007* (2013.01); *C12Y 301/00* (2013.01); *C12Y 605/01001* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. et al. |
| 4,458,066 A | 7/1984 | Caruthers et al. |
| 4,469,863 A | 9/1984 | Ts'o et al. |
| 4,476,301 A | 10/1984 | Imbach et al. |
| 4,845,205 A | 7/1989 | Huynh Dinh et al. |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |

(Continued)

OTHER PUBLICATIONS

Anderson, "Additive Effects of Alcohols and Polyols on Thermostability of Pepper Leaf Extracts," J. Am. Soc. Hort. Sci. 2007 132:67-72.

Beaucage et al., "Deoxynucleoside Phosphoramidites—A New Class of Key Intermediates for Deoxypolynucleotide Synthesis," Tetrahedron Lett. 1981 22:1859-1862.

Bhat et al., "Steric exclusion is the principal source of the preferential hydration of proteins in the presence of polyethylene glycols," Protein Sci. 1992 1:1133-1143.

Bounedjah et al., "Macromolecular Crowding Regulates Assembly of mRNA Stress Granules after Osmotic Stress," J. Biol. Chem. 2012 287:2446-2458.

Brown et al. "Chemical Synthesis and Cloning of a Tyrosine tRNA Gene," Meth. Enzymol. 1979 68:109-151.

(Continued)

*Primary Examiner* — Suzanne M Noakes
*Assistant Examiner* — Jae W Lee
(74) *Attorney, Agent, or Firm* — Klintworth & Rozenblat IP LLP

(57) ABSTRACT

The invention is directed to an in vitro method for joining a first set of double-stranded (ds) DNA molecules. Small molecules acting as chaperone agents are identified that promote efficient and rapid assembly (that is, joining) of overlapping double-stranded DNA fragments.

18 Claims, 13 Drawing Sheets

(56) References Cited

U.S. PATENT DOCUMENTS

| | | |
|---|---|---|
| 5,552,540 A | 9/1996 | Haralambidis |
| 5,561,225 A | 10/1996 | Maddry et al. |
| 5,563,253 A | 10/1996 | Agrawal et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Vveis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 7,776,532 B2 | 8/2010 | Gibson et al. |
| 9,534,251 B2 * | 1/2017 | Young .................. C12N 15/10 |

OTHER PUBLICATIONS

Englisch et al., "Chemically Modified Oligonucleotides as Probes and Inhibitors," Angewandte Chemie, International Ed. 1991 30(6):613-722.

Ghaghaei et al., "Comparison of the Chaperoning Action of Glycerol and β-Casein on Aggregation of Proteins in the Presence of Crowding Agent," Int. j. Peptide Res. Therap. 2011 17:101-111.

Goodchild, "Conjugates of oligonucleotides and modified oligonucleotides: a review of their synthesis and properties," Bloconjugate Chem. 1990 1(3):165-187.

Hatters et al., "Macromolecular Crowding Accelerates Amyloid Formation by Human Apolipoprotein C-II*," J. Biol. Chem. 2002 277:7824-7830.

Levy-Sakin et al., "The Influence of Chemical Chaperones on Enzymatic Activity under Thermal and Chemical Stresses: Common Features and Variation among Diverse Chemical Families," PLoS One 2014 9(2):e88541.

Metzker, "Sequencing technologies—the next generation," Nature Biotechnology Reviews 2010 11:31-46.

Minton, "The Influence of macromolecular Crowding and Macromolecular Confinement on Biochemical Reactions in Physiological Media," J. Biol. Chem. 2001 276(14):10577-10580.

Mishra et al., "Efficient Refolding of Aggregation-prone Citrate Synthase by Polyol Osmolytes," J. Biol. Chem. 2005 280:15553-15560.

Moody et al., "The Effects of the chaperone property of argentine (small molecule) and chemical chaperones glycerol and α-Crystallin in preventing aggregation of alpha-lactalbumin in the crowded system," Congress: 1st Tabriz Intl. Life Sci. Conf. and 12th Iran Biophys. Chem. Conf.

Narang et al., "Improved Phosphotriester Method for the Synthesis of Gene Fragments," Meth. Enzymol. 1979 68:90-99.

Nielsen et al., "Sequence-Selective Recognition of DNA by Strand Displacement with a Thymine-Substituted Polyamide," Science 1991 254:1497-1500.

Olsen et al., "Effects of osmolytes on hexokinase kinetics combined with macromolecular crowding Test of the osmolyte compatibility hypothesis towards crowded systems," Comp. Blochem. Physiol. A. Mol. Integr. Physiol. 2007 148:339-345.

Perlmutter, "Chemical Chaperones: A Pharmacological Strategy for Disorders of Protein Folding and Trafficking," Pediatr. Res. 2002 52:832-836.

Sanders et al., "Use of a macromolecular crowding agent to dissect interactions and define functions in transcriptional activation by a DNA-tracking protein: Bacteriophage T4 gene 45 protein and late transcription," Proc. Natl. Acad. Sci. U.S.A. 1994 91:7703-7707.

Sukenik et al., "Crowding Alone Cannot Account for Cosolute Effect on Amyloid Aggregation," PLoS One 2011 6:e15608.

Uversky, "Intrinsically Disordered Proteins and Their Environment: Effects of Strong Denaturants, Temperature, pH, Counter Ions, Membranes, Binding Partners, Osmolytes, and Macromolecular Crowding," Protein J. 2009 28:305-325.

Zancan et al., "Trehalose and glycerol stabilize and renature yeast inorganic pyrophosphatase inactivated by very high temperatures," Arch. Biochem. Biophys. 2005 444:52-60.

* cited by examiner

Step 1.

Step 2.

Step 3 and 4.

Step 5.

SEQUENCE LISTING

```
<160> NUMBER OF SEQ ID NOS: 34

<210> SEQ ID NO 1
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 1
atcagttctg gaccagcgag ctgt                                            24

<210> SEQ ID NO 2
<211> LENGTH: 23
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 2
atctgtcgcc cgtctcaaac gca                                             23

<210> SEQ ID NO 3
<211> LENGTH: 59
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 3
```

```
ggagggttgc gtttgagacg ggcgacagat ccatgggaat ggagggtatg ctgaaaggc      59
```

<210> SEQ ID NO 4
<211> LENGTH: 29
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 4

```
tagctgccag ataattggct tcacgaggc                                       29
```

<210> SEQ ID NO 5
<211> LENGTH: 59
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 5

```
cgcagcacag ctcgctggtc cagaactgat tagctgccag ataattggct tcacgaggc      59
```

<210> SEQ ID NO 6
<211> LENGTH: 27
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 6

```
tgcctcgtga agccaattat ctggcag                                         27
```

<210> SEQ ID NO 7
<211> LENGTH: 23
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 7

```
cagcgtatct tggccgcgaa gcg                                             23
```

<210> SEQ ID NO 8
<211> LENGTH: 53
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 8

```
cgcagcacag ctcgctggtc cagaactgat cagcgtatct tggccgcgaa gcg            53
```

<210> SEQ ID NO 9
<211> LENGTH: 54
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 9

```
ggagggttgc gtttgagacg ggcgacagat gaagggtacg acccggacct ggat           54
```

<210> SEQ ID NO 10
<211> LENGTH: 54
<212> TYPE: DNA
<213> ORGANISM: Artificial Sequence

```
-continued

<220> FEATURE:
<223> OTHER INFORMATION: SYNTHETIC OLIGONUCLEOTIDE

<400> SEQUENCE: 10
ttcgaaccgc ttcgcggcca agatacgctg aagggtacg acccggacct ggat          54

<210> SEQ ID NO 11
<211> LENGTH: 26
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 11
aacgtggacg aacatagccg tagcgc                                         26

<210> SEQ ID NO 12
<211> LENGTH: 56
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 12
cgcagcacag ctcgctggtc cagaactgat aacgtggacg aacatagccg tagcgc        56

<210> SEQ ID NO 13
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 13
ccgtgcgcta cggctatgtt cgtc                                           24

<210> SEQ ID NO 14
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 14
ttccgccact gcggtggcaa t                                              21

<210> SEQ ID NO 15
<211> LENGTH: 51
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 15
cgcagcacag ctcgctggtc cagaactgat ttccgccact gcggtggcaa t             51

<210> SEQ ID NO 16
<211> LENGTH: 23
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 16
ggtgtagcga ttgccaccgc agt                                            23
```

<210> SEQ ID NO 17
<211> LENGTH: 56
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 17
cgcagcacag ctcgctggtc cagaactgat ctcgaggcct ttcattgtgt ccagcg        56

<210> SEQ ID NO 18
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 18
acactgttac aggaatcttt gctg        24

<210> SEQ ID NO 19
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 19
cttccagctc caagaaatac gc        22

<210> SEQ ID NO 20
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 20
cgatccggga gcctttatgc        20

<210> SEQ ID NO 21
<211> LENGTH: 21
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 21
caggtcgttt ggcacaaact c        21

<210> SEQ ID NO 22
<211> LENGTH: 16
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 22
taaaacgacg gccagt        16

<210> SEQ ID NO 23
<211> LENGTH: 17
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 23
caggaaacag ctatgac                                                          17

<210> SEQ ID NO 24
<211> LENGTH: 477
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 24
ggagggttgc gtttgagacg ggcgacagat ccatgggaat ggagggtatg ctgaaaggcg      60
aaggacctgg tcctctccca ccgctgttac aacagtatgt cgaacttcgt gatcaatacc     120
cagattatct gcttttattc caggtcggcg atttttacga atgcttcggt gaggatgcag     180
agcgcctggc ccgtgccctt ggcctggtac tgacccacaa gacgtccaaa gactttacaa     240
cgcctatggc tggcatcccc ctccgtgcgt ttgaagctta cgccgagcgc ttattgaaaa     300
tgggctttcg tttggccgtc gctgaccaag tggaacccgc ggaggaagca aaggtctgg     360 tccgccgtga ggtgacccaa ctcctgacgc cgggcacact gttacaggaa tctttgctgc     420
ctcgtgaagc caattatctg gcagctaatc agttctggac cagcgagctg tgctgcg       477

<210> SEQ ID NO 25
<211> LENGTH: 447
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 25
ggagggttgc gtttgagacg ggcgacagat ccatgggaat ggagggtatg ctgaaaggcg      60
aaggacctgg tcctctccca ccgctgttac aacagtatgt cgaacttcgt gatcaatacc     120
cagattatct gcttttattc caggtcggcg atttttacga atgcttcggt gaggatgcag     180
agcgcctggc ccgtgccctt ggcctggtac tgacccacaa gacgtccaaa gactttacaa     240
cgcctatggc tggcatcccc ctccgtgcgt ttgaagctta cgccgagcgc ttattgaaaa     300
tgggctttcg tttggccgtc gctgaccaag tggaacccgc ggaggaagca aaggtctgg     360 tccgccgtga ggtgacccaa ctcctgacgc cgggcacact gttacaggaa tctttgctgc     420
ctcgtgaagc caattatctg gcagcta                                         447

<210> SEQ ID NO 26
<211> LENGTH: 437
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 26
tgcctcgtga agccaattat ctggcagcta tcgcgacggg cgacggctgg ggacttgcgt      60
ttttagacgt gtctaccggc gaatttaagg gtaccgtgct taagagcaaa tcagctctgt     120
acgacgaatt gttccgtcat cgccctgctg aagttctgtt agcccccgag ctgctcgaaa     180
atggtgcttt cctcgacgaa ttccgcaaac gctttccggt gatgctgtcc gaagccccgt     240
ttgagccgga aggtgagggt ccgctggccc tgccgtgc gcgcggtgca ctgctggcct      300
atgcgcaacg tacgcagggc ggtgctctga gcttgcagcc gtttcgtttc tacgatccgg     360

```
gagcctttat cgcctgccg gaagctacgt tacgtgcctt ggaagtgttc gaaccgcttc    420
gcggccaaga tacgctg                                                   437

<210> SEQ ID NO 27
<211> LENGTH: 467
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 27
tgcctcgtga agccaattat ctggcagcta tcgcgacggg cgacggctgg ggacttgcgt    60
ttttagacgt gtctaccggc gaatttaagg gtaccgtgct taagagcaaa tcagctctgt   120
acgacgaatt gttccgtcat cgccctgctg aagttctgtt agcccccgag ctgctcgaaa   180
atggtgcttt cctcgacgaa ttccgcaaac gctttccggt gatgctgtcc gaagcccgt    240 ttgagccgga aggtgagggt ccgctggccc tgcgccgtgc gcgcggtgca ctgctggcct   300
atgcgcaacg tacgcagggc ggtgctctga gcttgcagcc gtttcgtttc tacgatccgg   360
gagcctttat cgcctgccg gaagctacgt tacgtgcctt ggaagtgttc gaaccgcttc   420
gcggccaaga tacgctgatc agttctggac cagcgagctg tgctgcg                467

<210> SEQ ID NO 28
<211> LENGTH: 496
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 28
ggagggttgc gtttgagacg ggcgacagat ttcgaaccgc ttcgcggcca agatacgctg    60
gaagggtacg acccggacct ggatgccttg cgcgccgccc atcgtgaggg cgtcgcgtat   120
ttcttggagc tggaagagcg cgagcgtgaa cgcacgggta tccccacgct gaaagtaggc   180
tataacgctg tctttggcta ctacctcgaa gtaacccgcc cctactatga acgcgtccca   240
aaagaatatc gtccagttca gaccctgaaa gatcgtcagc gctacaccct cccggaaatg   300
aaagagaagg aacgtgaagt ctatcgtctg gaggcgttaa ttcgtcgccg ggaggaagag   360
gtgtttcttg aagttcgtga gcgggccaaa cgccaagccg aagcactgcg cgaagctgca   420
cgtattctgg ccgaactcga tgtctacgcc gctctggcgg aagttgccgt gcgctacggc   480
tatgttcgtc cacgtt                                                   496

<210> SEQ ID NO 29
<211> LENGTH: 466
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 29
ttcgaaccgc ttcgcggcca agatacgctg gaagggtacg acccggacct ggatgccttg    60
cgcgccgccc atcgtgaggg cgtcgcgtat ttcttggagc tggaagagcg cgagcgtgaa   120
cgcacgggta tccccacgct gaaagtaggc tataacgctg tctttggcta ctacctcgaa   180
gtaacccgcc cctactatga acgcgtccca aaagaatatc gtccagttca gaccctgaaa   240
gatcgtcagc gctacaccct cccggaaatg aaagagaagg aacgtgaagt ctatcgtctg   300
gaggcgttaa ttcgtcgccg ggaggaagag gtgtttcttg aagttcgtga gcgggccaaa   360
```

```
cgccaagccg aagcactgcg cgaagctgca cgtattctgg ccgaactcga tgtctacgcc    420
gctctggcgg aagttgccgt gcgctacggc tatgttcgtc cacgtt                  466

<210> SEQ ID NO 30
<211> LENGTH: 437
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 30
ccgtgcgcta cggctatgtt cgtccacgtt tcggcgaccg tctgcagatc cgcgcgggac     60
gtcacccagt ggttgagcgt cgcaccgagt ttgtgccaaa cgacctggaa atggcgcacg    120
agcttgtgct catcacaggg ccgaacatgg ctggcaaaag cactttcctg cgccagaccg    180
ccctgattgc actgttagcc caagtaggca gtttcgtgcc ggccgaagag gcgcacctgc    240
ctttattcga cgggatctat acccgtatcg gtgctagtga cgatctggcg ggaggtaaaa    300
gtactttcat ggtggaaatg gaggaagttg cgctgatttt gaaagaagca acggagaata    360
gtctggtgtt gcttgatgag gtggggcgcg gtacaagtag tttagatggt gtagcgattg    420
ccaccgcagt ggcggaa                                                    437

<210> SEQ ID NO 31
<211> LENGTH: 467
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 31
ccgtgcgcta cggctatgtt cgtccacgtt tcggcgaccg tctgcagatc cgcgcgggac     60
gtcacccagt ggttgagcgt cgcaccgagt ttgtgccaaa cgacctggaa atggcgcacg    120
agcttgtgct catcacaggg ccgaacatgg ctggcaaaag cactttcctg cgccagaccg    180
ccctgattgc actgttagcc caagtaggca gtttcgtgcc ggccgaagag gcgcacctgc    240
ctttattcga cgggatctat acccgtatcg gtgctagtga cgatctggcg ggaggtaaaa    300
gtactttcat ggtggaaatg gaggaagttg cgctgatttt gaaagaagca acggagaata    360
gtctggtgtt gcttgatgag gtggggcgcg gtacaagtag tttagatggt gtagcgattg    420
ccaccgcagt ggcggaaatc agttctggac cagcgagctg tgctgcg                 467

<210> SEQ ID NO 32
<211> LENGTH: 453
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 32
ggtgtagcga ttgccaccgc agtggcggaa gcccttcacg aacgtcgcgc atataccttt     60
tttgcgaccc actattttga acttactgcg ttgggtcttc cgcgcctgaa aaatctgcac    120
gtagccgctc gcgaagaagc gggtggactg gtctttatc atcaagtgct gccgggcccg    180
gcgagtaaaa gttacggcgt tgaggtagcg gcaatggcag ggctgcctaa agaagtcgtg    240
gctcgtgccc gcgccttgct tcaggcaatg ccgctcgcc gtgaaggtgc attggatgca    300
gtgttagaac gtctgttagc acttgatcct gaccgcttga ccccgcttga agcgttacgt    360
```

```
ctgcttcagg agctgaaagc tctggcgttg ggagccccgc tggacacaat gaaaggcctc      420
gagatcagtt ctggaccagc gagctgtgct gcg                                  453

<210> SEQ ID NO 33
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 33
gattaagttg ggtaacgcca gg                                              22

<210> SEQ ID NO 34
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 34
ctatgaccat gattacgcca cgag                                            24
```

EFFICIENT AND RAPID METHOD FOR ASSEMBLING AND CLONING DOUBLE-STRANDED DNA FRAGMENTS

CROSS-REFERENCE TO RELATED APPLICATIONS

This application claims benefit of priority under 35 U.S.C. 119 to U.S. provisional patent application Ser. No. 62/025,822, filed Jul. 17, 2014, and entitled "EFFICIENT AND RAPID METHOD FOR ASSEMBLING AND CLONING DOUBLE-STRANDED DNA FRAGMENTS," the contents of which are herein incorporated by reference in its entirety.

SEQUENCE LISTING

The instant application contains a Sequence Listing that has been submitted in both PDF and ASCII format via EFS-Web and is hereby incorporated by reference in its entirety. The ASCII copy, created on Jul. 17, 2015, is named IDT01-007-US_ST25.txt, and is 12,109 bytes in size.

FIELD OF THE INVENTION

This invention relates to methods for in vitro recombination of nucleic acids. In particular, small molecules acting as chaperone agents are identified that promote efficient and rapid assembly (that is, joining) of overlapping double-stranded DNA fragments.

BACKGROUND OF THE INVENTION

Nucleic acid recombination in vitro lies at the core of molecular biology and biotechnology. The efficiency whereby recombinant nucleic acid technology is achieved can dictate the outcome of certain biotechnology implementations. For example, the cloning of recombinant DNA molecules is dramatically enhanced by several orders of magnitude when the overlapping fragments are annealed together via sticky ends and ligated with a ligase enzyme in vitro as compared to blunt-ended fragments ligated under similar condition. Likewise, fragments having significant overlap (for example, G/C- or A/T-tailed fragments) can result in successful transformation and cloning of recombinant fragments without ligation in vitro prior to transformation, wherein the resultant transformed molecules are repaired and ligated together inside cells following transformation. Yet the use of ligase reactions in vitro to form joined products prior to transformation dramatically increases the efficiency of cloning molecules containing overlap regions.

More complex recombinant ligations, such as the assembly and ligation of a plurality of recombinant fragments into a vector, necessitates the use of ligase reactions to ensure acceptable cloning efficiencies of the resultant recombinant products. In one implementation, Gibson et al. describe in U.S. Pat. No. 7,776,532 ("the '532 patent"), entitled METHOD FOR IN VITRO RECOMBINATION, a method for directed assembly and ligation of a plurality of recombinant fragments. The method relies on the use of isolated protein reagents for joining two double-stranded (ds) DNA molecules of interest, wherein the distal region of the first DNA molecule and the proximal region of the second DNA molecule share a region of sequence identity. The first step includes chewing back the DNA molecules with an enzyme having an exonuclease activity, to yield single-stranded overhanging portions of each DNA molecule that contain a sufficient length of the region of sequence identity to hybridize specifically to each other. The second step includes specifically annealing the single-stranded overhangs. The third step includes repairing single-stranded gaps in the annealed DNA molecules and sealing the nicks thus formed (that is, ligating the nicked DNA molecules). The region of sequence identity generally typically includes at least 20 non-palindromic nucleotides (nt), such as at least about 40 non-palindromic nt. A crowding agent is present during all steps of the reaction, and/or the repair reaction is achieved with Taq DNA polymerase and a compatible ligase, such as Taq DNA ligase. The method allows the joining of a number of DNA fragments, in a predetermined order and orientation, without the use of restriction enzymes. It can be used, for example, to join synthetically produced sub-fragments of a gene or genome of interest.

Crowding Agents

The '532 patent defines a crowding agent as a compound that allows for, enhances or facilitates molecular crowding. The '532 patent provides examples of crowding agents as macromolecular polymer species such as polyethylene glycol (PEG 200 and up, including 20,000 and up); Ficoll, such as Ficoll 70; dextran, such as dextran 70; or the like. The '532 patent teaches that a crowding agent provides molecular crowding to bind to and tie up water in a solution, thereby removing water from components suspended in solution to allow components of the solution to come into closer contact with one another.

The '532 patent teaching about crowding agents is also consistent with and supported by that found in the literature. Bhat R & Timasheff S N in *Protein Sci.* 1992 1:1133-43 describe the crowding effect of polyethylene glycol on proteins by affecting the hydration state of the proteins. Hatters D M et al. in *J. Biol. Chem.* 2002 277:7824-30 examine the effect of excluded volume on aggregation using concentrated solution of dextran. Minton A P in *J. Biol. Chem.* 2001 276:10577-80 reviews the effect of crowding on enzyme activity. Sanders G M et al. in *Proc. Natl. Acad. Sci. U.S.A.* 1994 91:7703-7 describe the use of the crowding agents polyethylene glycol, polyvinyl alcohol, dextran, and Ficoll to enhance in vitro transcription.

Chaperone Agents

The literature teaches a class of small molecules having chaperone activity that differ from the function of crowding agents, such as those described in the '532 patent. The literature suggests that chaperone agents have the opposite affects of crowding agents, as described below.

Anderson, J A, in *J. Am. Soc. Hort. Sci.* 2007 132:67-72 describes polyols, as well as sugars, amino acids and methylamines as chemical chaperones that stabilize proteins in response to stress such as high temperature. Anderson provides examples of chemical chaperones having such activity to include mannitol, glycerol, trehalose, maltose, sucrose, glycine, betaine and trimethylamine.

Bounedjah O. et al. in *J. Biol. Chem.* 2012 287:2446-58 states that osmolytes (that include chaperones) serve a protective function and reduce the effects of macromolecular crowding. These authors identify betaine, taurine, and myo-inositol as having such protective functions to reducing macromolecular crowding.

Ghahghaei A et al. in *Int. J. Peptide Res. Therap.* 2011 17:101-11 states that glycerol is a chemical chaperone belonging to the polyol family that increases protein stability and inhibits protein aggregation. These authors describe β-casein as a molecular chaperone and differentiate these compounds from crowding agents such as dextran.

Levy-Sakin M et al. in *PLoS One* 2014 9:e88541 describes glycerol and other polyols as chaperones and protein stabilizers. These authors state that small carbohydrates have the same effect and studied the ability of ethylene glycol, glycerol, D-theritol, meso-erythritol, D-adonitol, L-arabitol, xylitol, D-sorbitol and D-mannitol to stabilize the activity of trypsin under stress.

Mishra R et al. in *J. Biol. Chem.* 2005 280:15553-60 describe the ability of glycerol to suppress protein aggregation. These authors define polyethylene glycol as a "viscogen" that suppresses protein folding (that leads to aggregation).

Moody M et al. in *1st Tabriz Intl. Life Sci. Conf* & *12th Iran Biophys. Chem. Conf.* state that glycerol and arginine are both chemical chaperones known to stabilize protein conformation and prevent aggregation in a crowded environment created by the presence of dextran.

Olsen S N, et al. in Comp. *Biochem. Physiol. A. Mol. Integr. Physiol.* 2007 148:339-45. These authors studied the effect of osmolytes on enzyme activity in combination with macromolecular crowding.

Perlmutter D H in *Pediatr Res.* 2002 52:832-6 describes polyols (glycerol), trimethylamines and amino acid derivatives as chemical chaperones.

Sukenik S et al. in *PLoS One* 2011 6:e15608 shows that osmolytes stabilize the monomeric state of amyloid, but also stabilizes the fibril once it is formed.

Uversky V N in *Protein J.* 2009 28:305-25 shows that the osmolytes proline, sarcosine and sorbitol (a polyol) effectively induced protein folding.

Zancan P & Sola-Penna M. in *Arch. Biochem. Biophys.* 2005 444:52-60 demonstrates that trehalose and glycerol can function as chemical chaperones.

The '532 patent does not recite that crowding agents include chaperones and osmolytes or examples of the same, such as glycerol and the other small molecules describe in the literature. For this reason—and owing to the possible confusing overlap between these apparently distinct classes of compounds having disparate effects on mixtures of nucleic acids and nucleic acid-modifying enzymes, there remains to be established whether small molecules acting as chaperones have any effect on nucleic acids and nucleic acid modifying enzymes directed to in vitro recombination of overlapping double-stranded fragments in assembling reactions.

BRIEF SUMMARY OF THE INVENTION

In one aspect, an in vitro method for joining a first set of double-stranded (ds) DNA molecules is provided. The method includes several steps. The first step includes providing two or more dsDNA molecules to be joined in a reaction mixture, wherein, for each pair of dsDNA molecules to be joined, a distal region of a first DNA molecule and a proximal region of a second DNA molecule share a region of sequence homology. The second step includes treating the provided dsDNA molecules with a substantially purified enzyme having exonuclease activity, whereby a single-stranded overhanging portion is generated in each of the dsDNA molecules by exonuclease digestion, wherein each overhanging portion contains the region of homology or a portion thereof sufficient to specifically anneal to the overhanging portion in the other molecule of the pair. The third step includes incubating the DNA molecules generated in the second step, under conditions whereby they anneal through the regions of homology or portions thereof. The fourth step includes treating the annealed molecules with a substantially purified polymerase and a substantially purified compatible ligase, under conditions whereby remaining single-stranded gap(s) are filled in by the polymerase and nicks are sealed by the ligase, thereby joining the dsDNA molecules. A chaperone agent is present in the reaction mixture during each of second step, third step and fourth step.

In a second aspect, a composition for joining a first set of double-stranded (ds) DNA molecules is provided. The composition includes the following: (a) an isolated enzyme that exhibits a 3' or 5' exonuclease activity; (b) a non strand-displacing DNA polymerase; (c) a DNA ligase that is compatible with the DNA polymerase in (b); and (d) a chaperone agent.

In a third aspect, a kit for joining a first set of double-stranded (ds) DNA molecules is provided. The kit includes the following: (a) an isolated enzyme having a 3' or 5' exonuclease activity; (b) an isolated non strand-displacing DNA polymerase; (c) an isolated ligase that is compatible with the isolated non strand-displacing polymerase of (b); and (d) a reagent solution comprising a chaperone agent.

In a fourth aspect, an in vitro method for joining a first set of double-stranded (ds) DNA molecules is provided. The method includes several steps. The first step includes providing two or more dsDNA molecules to be joined in a reaction mixture. For each pair of dsDNA molecules to be joined, a distal region of a first DNA molecule and a proximal region of a second DNA molecule share a region of sequence homology; a single-stranded overhanging portion is present in each of the dsDNA molecules; and each overhanging portion contains the region of homology or a portion thereof sufficient to specifically anneal to the overhanging portion in the other molecule of the pair. The second step includes incubating the DNA molecules of the first step under conditions whereby they anneal through the regions of homology or portions thereof. The third step includes treating the annealed molecules with an optional, substantially purified polymerase and a substantially purified compatible ligase under conditions whereby remaining single-stranded gap(s) are filled in by the polymerase and nicks are sealed by the ligase; thereby joining the dsDNA molecules. A chaperone agent is present in the reaction mixture during each of second step and the third step.

In a fifth aspect, a composition for joining a first set of double-stranded (ds) DNA molecules is provided. The composition includes the following: (a) an optional non strand-displacing DNA polymerase; (b) a DNA ligase that is compatible with the DNA polymerase in (b); and (c) a chaperone agent.

In a sixth aspect, a kit for joining a first set of double-stranded (ds) DNA molecules is provided. The kit includes the following: (a) an optional isolated non strand-displacing DNA polymerase; (b) an isolated ligase that is compatible with the isolated non strand-displacing polymerase of (a); and (c) a reagent solution comprising a chaperone agent.

DETAILED DESCRIPTION OF THE INVENTION

Figure 1:
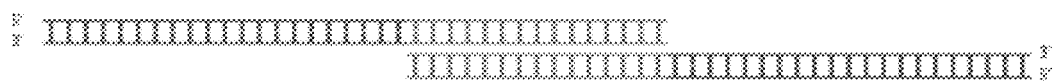
FIG. 1 depicts a typical isothermal assembly method for double-stranded DNA. The following events can take place in a single 50° C. reaction: (1) individual segments of dsDNA are designed so that the 3' strands have complementary overlaps; (2) a mesophilic 5' exonuclease briefly digests into the 5' ends of the doublestranded DNA fragments before being inactivated at 50° C.; (3) the newly generated complementary 3' overhangs anneal; (4) a high fidelity DNA polymerase fills in gaps completing fragment-containing circular plasmids and leaving free ends retracted on linear fragments; (5) finally, a thermophilic DNA ligase covalently joins DNA segments.
Figure 1:
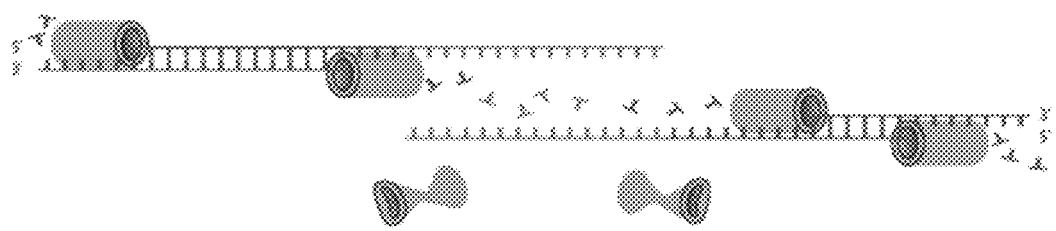
Figure 1:
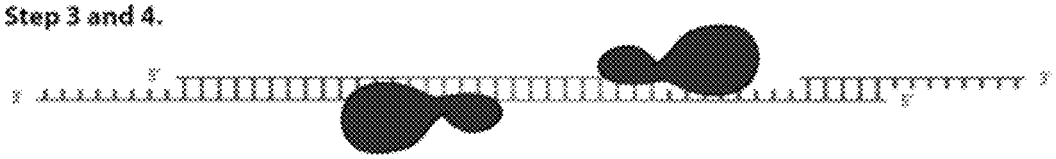
Figure 1:
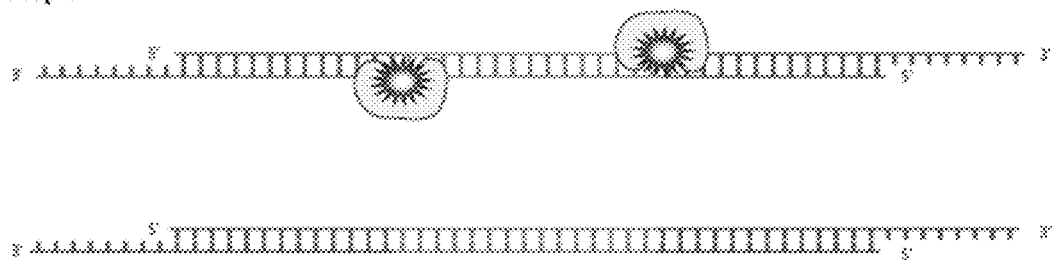

Certain terms are first defined. Additional terms are defined throughout the specification.

Terms used herein are intended as "open" terms (for example, the term "including" should be interpreted as "including but not limited to," the term "having" should be interpreted as "having at least," the term "includes" should be interpreted as "includes but is not limited to," etc.).

Furthermore, in those instances where a convention analogous to "at least one of A, B and C, etc." is used, in general such a construction is intended in the sense of one having ordinary skill in the art would understand the convention (for example, "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "from," "to," "up to," "at least," "greater than," "less than," and the like, include the number recited and refer to ranges that can subsequently be broken down into sub-ranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the articles "a" and "an" refer to one or to more than one (for example, to at least one) of the grammatical object of the article.

As used herein, the singular forms "a," "an," and "the" include plural referents unless the context clearly dictates otherwise.

As used herein, "or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"About" and "approximately" shall generally mean an acceptable degree of error for the quantity measured given the nature or precision of the measurements. Exemplary degrees of error are within 25 percent (%), typically, within 10%, and more typically, within 5% of a given value or range of values.

The term "crowding agent" refers to a compound that allows for, enhances or facilitates molecular crowding. A crowding agent that allows for molecular crowding, binds to and ties up water in a solution, thereby allowing components of the solution to come into closer contact with one another. For example, DNA molecules to be recombined can come into closer proximity when a crowding agent is included in the mixture, thereby facilitating the annealing of the single-stranded overhangs. Enzyme can come into closer contact with their DNA substrates by the removal of water molecules. Crowding agents can reduce the volume of the solvent in a reaction, resulting in an apparent increase in protein concentration. Crowding agents are further described as macromolecules, with their effectiveness related to their size (Minton A P (2001) *J. Biol. Chem.* 276 (14): 10577-80). Examples of crowding agents include a variety of well-known macromolecules, such as polymers, for example, polyethylene glycol (PEG 200 and up, including 20,000 and up); Ficoll, such as Ficoll 70; dextran, such as dextran 70; or the like.

The term "chaperone agent" refers to a compound that stabilizes a mixture of nucleic acids and proteins without allowing for, enhancing or facilitating molecular crowding in a mixture. Accordingly, a chaperone agent refers to a compound devoid of crowding agent activity. When a chaperone agent is present in a mixture containing a plurality of nucleic acids under conditions competent for in vitro recombination of the plurality of nucleic acids, the chaperone agent provides for enhanced in vitro recombination of nucleic acids in the mixture. Examples of a chaperone agent include glycerol, D-mannitol, D-theritol, meso-erythritol, D-adonitol, L-arabitol, D-sorbitol, xylitol, trehalose, maltose, sucrose, glycine, betaine, taurine, β-casein, arginine, proline, sarcosine, sorbitol, myo-inositol and trimethylamine, among others. A chaperone agent is structurally distinct from a crowding agent, because examples of a chaperone agent are small molecules lacking polymeric form whereas examples of a crowding agent are macromolecular polymers. Chaperone agents are classified as small molecule agents that can stabilize or renature proteins and prevent them from becoming denatured and hence inactive. As used herein, chaperone agents exclude proteins. As used herein, chaperone agent and chaperone have the same meaning and are used interchangeably.

The term, an "isolated" protein, as used herein, means that the protein is removed from its original environment (for example, the natural environment if it is naturally occurring), and isolated or separated from most other component with that it is naturally associated. For example, a naturally-occurring protein present in its natural living host (for example, a bacteriophage protein present in a bacterium that has been infected with the phage) is not isolated, but the same protein, separated from some or all of the coexisting materials in the natural system, is isolated. Such proteins can be part of a composition or reaction mixture, and still be isolated in that such composition or reaction mixture is not part of its natural environment. The term "an isolated protein," as used herein, can include 1, 2, 3, 4 or more copies of the protein, i.e., the protein can be in the form of a monomer, or it can be in the form of a multimer, such as dimer, trimer, tetramer or the like, depending on the particular protein under consideration. In some embodiments, the protein is purified. Methods for purifying the proteins used in methods of the invention are conventional. In some embodiments, the protein is substantially purified or is purified to homogeneity. By "substantially purified" is meant that the protein is separated and is essentially free from other proteins, i.e., the protein is the primary and active constituent. The purified protein can then be contacted with the DNAs to be joined. Proteins used in the methods of the invention can be in the form of "active fragments," rather than the full-length proteins, provided that the fragments retain the activities (enzymatic activities or binding activities) required to achieve the joining. One of skill in the art will recognize how to make and use such active fragments.

Compositions that include liquid components (for example, glycerol) are specified in percentages in terms of weight to volume (wt/vol or w/v), unless the context dictates otherwise (for example, molar concentration).

"Member" or "library member" or other similar term, as used herein, refers to a nucleic acid molecule, for example, a DNA, RNA, or a combination thereof that is the member of a library. Typically, a member is a DNA molecule, for example, genomic DNA or cDNA. A member can be fragmented, for example, sheared or enzymatically prepared, genomic DNA. Members comprise sequence from a subject and can also comprise sequence not derived from the subject, for example, a non-target sequence such as adaptors sequence, a primer sequence, or other sequences that allow for identification, for example, "barcode" or "index" sequences.

"Next-generation sequencing or NGS or NG sequencing" as used herein, refers to any sequencing method that determines the nucleotide sequence of either individual nucleic acid molecules (for example, in single molecule sequencing) or clonally expanded proxies for individual nucleic acid molecules in a high through-put fashion (for example, greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, for example, in Metzker, M. (2010) *Nature Biotechnology Reviews* 11:31-46, incorporated herein by reference.

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in that the base, sugar or phosphate backbone is modified as well as non-purine or non-pyrimidine nucleotide analogs.

The term "nucleic acid target" refers to the nucleic acid having complementarity with a primer.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in that synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature. Primer extension can also be carried out in the absence of one or more of the nucleoside triphosphates in that case an extension product of limited length is produced. As used herein, the term "primer" is intended to encompass the oligonucleotides used in ligation-mediated reactions, in that one oligonucleotide is "extended" by ligation to a second oligonucleotide that hybridizes at an adjacent position. Thus, the term "primer extension", as used herein, refers to both the polymerization of individual nucleoside triphosphates using the primer as a point of initiation of DNA synthesis and to the ligation of two oligonucleotides to form an extended product.

A primer is preferably a single-stranded DNA. The appropriate length of a primer depends on the intended use of the primer but typically ranges from 6 to 50 nucleotides, preferably from 15-35 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features that allow for the detection or immobilization of the primer but do not alter the basic property of the primer that of acting as a point of initiation of DNA synthesis. For example, primers may contain an additional nucleic acid sequence at the 5' end that does not hybridize to the nucleic acid target, but that facilitates cloning or detection of the amplified product. The region of the primer that is sufficiently complementary to the template to hybridize is referred to herein as the hybridizing region.

"Sample," "tissue sample," "patient sample," "patient cell or tissue sample" or "specimen," each refers to a collection of similar cells obtained from a tissue, or circulating cells, of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, for example, an FFPE block or a frozen sample.

The term "biological sample" refers to a material obtained from a biological source. Examples of a biological sample include a cell, a tissue, a fluid (for example, blood), an excrement (for examples, feces or urine), a biopsy, a swab, and a skin scraping, among others. Biological samples include "Sample," "tissue sample," "patient sample," "patient cell or tissue sample" or "specimen," as those terms are used herein.

"Sensitivity," as used herein, is a measure of the ability of a method to detect a preselected sequence variant in a heterogeneous population of sequences. A method has a sensitivity of S % for variants of F % if, given a sample in that the preselected sequence variant is present as at least F % of the sequences in the sample, the method can detect the preselected sequence at a preselected confidence of C %, S % of the time. By way of example, a method has a sensitivity of 90% for variants of 5% if, given a sample in that the preselected variant sequence is present as at least 5% of the sequences in the sample, the method can detect the preselected sequence at a preselected confidence of 99%, 9 out of 10 times (F=5%; C=99%; S=90%). Exemplary sensitivities include those of S=90%, 95%, 99% for sequence variants at F=1%, 5%, 10%, 20%, 50%, 100% at confidence levels of C=90%, 95%, 99%, and 99.9%.

"Specificity," as used herein, is a measure of the ability of a method to distinguish a truly occurring preselected sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or members of a gene family. A method has a specificity of X % if, when applied to a sample set of $N_{Total}$ sequences, in that $X_{True}$ sequences are truly variant and $X_{Not\ true}$ are not truly variant, the method selects at least X % of the not truly variant as not variant. For example, a method has a specificity of 90% if, when applied to a sample set of 1,000 sequences, in that 500 sequences are truly variant and 500 are not truly variant, the method selects 90% of the 500 not truly variant sequences as not variant. Exemplary specificities include 90, 95, 98, and 99%.

A "control nucleic acid sample" or "reference nucleic acid sample" as used herein, refers to nucleic acid molecules from a control or reference sample. Typically, it is DNA, for example, genomic DNA, RNA, or cDNA derived from RNA, not containing the alteration or variation in the gene or gene product. In certain embodiments, the reference or control nucleic acid sample is a wild type or a non-mutated sequence. In certain embodiments, the reference nucleic acid sample is purified or isolated (for example, it is removed from its natural state). In other embodiments, the reference nucleic acid sample is from a non-tumor sample, for example, a blood control, a normal adjacent tumor (NAT), or any other non-cancerous sample from the same or a different subject. In some embodiments, the reference nucleic acid sample can be a marked RNA that permits detection of the efficiency of a method for selecting an unmarked RNA.

"Sequencing" a nucleic acid molecule requires determining the identity of at least 1 nucleotide in the molecule. In embodiments the identity of less than all of the nucleotides in a molecule are determined. In other embodiments, the identity of a majority or all of the nucleotides in the molecule is determined.

DNAs used in methods of the invention can have one or more modified nucleotides. For example, they may contain one or more modifications to either the base, sugar, or phosphate moieties. Modifications to the base moiety would include natural and synthetic modifications of A, C, G, and T as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al. (1991) Angewandte Chemie, International Edition 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Base modifications often can be combined with for example a sugar modification, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941 that detail and describe a range of base modifications.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)—OCH$_3$, —O(CH$_2$)$_n$NH$_2$, —O(CH$_2$)$_n$CH$_3$, —O(CH$_2$)$_n$ONH$_2$, and —O(CH$_2$)$_n$ON[(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkyl-phosphonates, thionoalkyl-phosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

It is understood that nucleotide analogs need only contain a single modification, but may also contain multiple modifications within one of the moieties or between different moieties.

Nucleotide substitutes are nucleotides or nucleotide analogs that have had the phosphate moiety and/or sugar moieties replaced. Nucleotide substitutes include molecules having similar functional properties to nucleotides, but that do not contain a phosphate moiety, such as peptide nucleic acid (PNA). Nucleotide substitutes include molecules that will recognize and hybridize to complementary nucleic acids in a Watson-Crick or Hoogsteen manner, but that are linked together through a moiety other than a phosphate moiety. Nucleotide substitutes are able to conform to a double helix type structure when interacting with the appropriate target nucleic acid.

Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate back-bones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules. See also Nielsen et al. (1991) Science 254:1497-1500.

DNA molecules of the invention can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, 2'-O-methyl ribonucleotides, or a mixture of ribonucleotides and 2'-O-methyl ribonucleotides. The nucleotides can be comprised of bases (that is, the base portion of the nucleotide) and can comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

Headings, for example, (a), (b), (i) etc., are presented merely for ease of reading the specification and claims. The use of headings in the specification or claims does not require the steps or elements be performed in alphabetical or numerical order or the order in that they are presented.

The present inventors have identified combinations of isolated proteins (for example, enzymes) and suitable reaction conditions employing chaperone agents for the efficient in vitro joining of two or more double-stranded DNA molecules that share overlapping regions of sequence homology (for example, sequence identity) at their ends. In brief, the method comprises (1) a "chew-back" step, in that an exonuclease chews back ends of the double-stranded DNA molecules, to expose single-stranded overhangs comprising the regions of overlap; (2) an annealing step, in that the single-stranded overhangs are annealed (hybridized) specifically; and (3) a repair step, in that remaining single-stranded gaps in the annealed molecules are filled in and nicks thus formed are sealed (ligated). The region of sequence homology generally comprises at least about 20 non-palindromic nucleotides (nt), for example, at least about 40 non-palindromic nt. A "single-stranded gap," as used herein, refers to a single-stranded region of a nucleic acid wherein the surrounding regions are double-stranded. The method allows, for example, for the joining of DNA molecules of interest to one another in a predefined order and orientation, without the use of (or with very limited use of) restriction enzymes.

The chaperone agent can be included in any one or each of the foregoing steps of the method outlined above and described elsewhere herein. A variety of suitable chaperone agents will be evident to one having ordinary skill in the art. These include a variety of well-known small molecules, such as glycerol, D-mannitol, D-theritol, meso-erythritol, D-adonitol, L-arabitol, D-sorbitol, xylitol, trehalose, maltose, sucrose, glycine, betaine, taurine, β-casein, arginine, proline, sarcosine, sorbitol, myo-inositol and trimethylamine, among others. Much of the discussion herein is directed to glycerol or D-Sorbitol as exemplary chaperone agents. However, the discussion is meant also to apply to other suitable chaperone agents. A person having ordinary skill in the art will recognize how to implement routine changes in the method in order to accommodate the use of other chaperone agents.

In one embodiment of this method, an enzyme having a 3→5' exonuclease activity generates 5' single-stranded overhangs in each of two DNA molecules to be joined, wherein the single-stranded overhangs comprise the region of sequence homology (for example, identity). The two single-stranded overhangs anneal to form a gapped molecule; a DNA polymerase fills in the gaps; and a ligase seals the nicks. This embodiment of the method is illustrated schematically in FIG. 1. In another embodiment of the method, the enzyme in the first step has a 5→3' exonuclease activity, and 3' single-stranded overhangs are generated and then joined. A variety of different enzymes can be used in the different steps of the method.

The "joining" of two DNA molecules is sometimes referred to herein as "recombination" of the two DNA molecules. In the method of the invention, the proteins having exonuclease, polymerase and ligase activities are isolated (for example, substantially purified); cell extracts or intact cells are not employed.

The method can be used to join more than two DNA molecules. To accomplish this, the DNA molecules to be joined are designed such that, for each pair of DNA molecules to be joined, the distal region of one DNA molecule comprises a region of sequence homology (for example, identity) with the proximal region of the other DNA molecule. To facilitate the joining of the DNA molecules in a predetermined orientation and order, each set of distal and proximal regions of sequence identity is selected (designed) to be unique (to be different from the regions of sequence identity of the other pairs of DNA molecules). The method allows a number of DNA molecules to be joined (for example, in a single reaction mixture, and a single tube).

In one embodiment, the DNA molecules that are joined are synthetically generated DNA molecules that lie adjacent to one another in a gene or genome of interest. For example, a first set of about 4-8 such DNA molecules having a range from about 120 basepairs to about 6 kilobase pairs (kb) each can be joined in the proper order and orientation according to a method of the invention. A second set of a similar number of adjoining DNA molecules of about the same size is also joined; and then, in a second stage assembly, the two sets of joined molecules are joined to one another. The process is repeated with further sets of DNA molecules, in as many cycles as desired. In such a manner, the component elements of a gene, gene pathway or genome, all or nearly all of which have been generated synthetically, can be joined in sequential steps to form a complete gene or genome.

A method of the invention can be used to join any DNA molecules of interest, including DNAs that are naturally occurring, cloned DNA molecules, synthetically generated DNAs, etc. The joined DNA molecules may, if desired, be cloned into a vector (for example, using a method of the invention).

Advantages of the method of the invention include the ability to perform the joining (recombination) reactions under well-defined conditions, using well-characterized, isolated (for example, substantially purified) proteins (for example, enzymes). This allows the joining reactions to be controlled and reproducible. In a method of the invention, the joining process is not subject to competing reactions brought about by other enzymes in the reaction mixture, such as exonucleases and endonucleases that can be present in cells or cell extracts. The method of the invention requires very little sample handling and can be completed rapidly (for example, within 1-2 hrs). In some embodiments, the joining of a desired set of nucleic acid molecules is performed in a single vessel, such as a tube in a thermocycler apparatus. If a thermocycler is used, a researcher only needs to be present, for example, to initiate the chew-back reaction and to add the repair mix after the annealing process is complete. If desired, the steps of the method can be carried out robotically, without the intervention of an investigator, allowing for high throughput joining (assembly) to occur.

The ability to join DNA molecules in a defined order and orientation allows, for example, for the cloning of one or more fragments of interest into a linearized vector in a defined orientation; or for the assembly of component DNA portions of a longer sequence of interest (such as the assembly of component parts of a synthetic gene or genome); or for the assembly and cloning of sub-fragments of a DNA that are too large to clone using a PCR amplification step. The method allows one to join and/or clone DNA molecules of interest without having to rely on the presence of restriction enzyme recognition sites at the ends of the fragments to be joined. The in vitro procedure also allows one to assemble DNAs that are unstable or otherwise recalcitrant to in vivo cloning, and thus would be difficult to clone by a method requiring transformation into and replication in a bacterium. If desired, DNAs assembled by a method of the invention can then be amplified in vitro (for example, by multiple displacement amplification (MDA), such as rolling circle amplification (RCA); or by PCR), again without having to passage the DNA through a bacterium.

One aspect of the invention is an in vitro method, using isolated (for example, substantially purified) proteins, for joining two or more double-stranded (ds) DNA molecules of interest, wherein the distal region of the first DNA molecule and the proximal region of the second DNA molecule of each pair share a region of sequence identity, comprising
  (a) treating the DNA molecules with an enzyme having an exonuclease activity, under conditions effective to yield single-stranded overhanging portions of each DNA molecule that contain a sufficient length of the region of sequence homology to hybridize specifically to the region of sequence homology of its pair;
  (b) incubating the treated DNA molecules of (a) under conditions effective to achieve specific annealing of the single-stranded overhanging portions; and
  (c) treating the incubated DNA molecules in (b) under conditions effective to fill in remaining single-stranded gaps and to seal the nicks thus formed.

In one aspect of the invention, the region of sequence identity comprises at least about 20, 30 or 40 non-palindromic nucleotides (nt), for example, at least about 80, 300 or 500 nt.

In one aspect of the method, a chaperone agent (such as glycerol, for example, at a concentration of about 6%-8.5%, or D-Sorbitol, for example at a concentration of about 0.25 M-1.50 M) is present in the reaction mixture at each of steps (a), (b) or (c); and/or, in (c) the DNA molecules are treated with Taq DNA polymerase and a compatible ligase, such as Taq ligase.

In (a), the enzyme may have a 3→5' exonuclease activity (for example, an exonuclease, such as exonuclease III; or a DNA polymerase, such as T4 DNA polymerase, T7 DNA polymerase, DNA polymerase I, Klenow DNA polymerase, Phi 29 DNA polymerase, Pfu polymerase, Phusion™ High-Fidelity polymerase, Vent$_R$, Deep Vent$_R$, or 9° N$_m$ DNA polymerase that exhibits exonuclease activity when it is incubated under suitable conditions, such as the absence of added dNTPs).

In (a), the enzyme may have a 5→3' exonuclease activity (for example, an exonuclease, such as phage T5 exonuclease, phage T7 exonuclease, phage lambda exonuclease, Redα of lambda phage, or RecE of Rac prophage).

In (b), the treated molecules of (a) may be incubated (for example, at about 75° C.) under conditions effective to separate the strands of the overhangs that have annealed and, optionally, to inactivate the enzyme, and then slowly cooled to about 24° C. (for example, about 23° C.) or less, under conditions effective to allow the single-stranded overlaps to anneal.

In (c), the conditions effective to fill in remaining single-stranded gaps and to seal the nicks may comprise incubating the annealed DNA molecules with a DNA polymerase in the presence of dNTPs and a compatible ligase. In one embodiment, the DNA polymerase is T4, T7, E. coli Pol I, Klenow, Taq, Phusion™ or Pfu polymerase; the ligase is T4, E. coli or Taq DNA ligase or Ampligase; and the treatment is performed at about 37° C. In another embodiment, the DNA polymerase is Taq, Phusion™ or Pfu DNA polymerase; the ligase is Taq DNA ligase or Ampligase; and the treatment is performed at about 45° C.

One aspect of the invention is an in vitro method, using isolated (for example, substantially purified) proteins, for joining at least two ds DNA molecules of interest, each of about 120 basepairs to about 6 kilobasepairs (kb), wherein the distal region of the first DNA molecule and the proximal region of the second DNA molecule of each pair share a unique region of sequence identity, comprising
  (a) treating approximately equimolar amounts of the DNA molecules with T4 DNA polymerase at about 37° C., in a solution comprising about 0.2 M Tris at about pH 7.5, in the absence of added dNTPs, under conditions effective to chew-back at least the regions of sequence identity in each molecule, thereby forming single-stranded overhanging ends of sufficient length to hybridize specifically to overhangs having the complement of the shared region of sequence identity;
  (b) annealing the treated DNA molecules in (a) by incubating them at about 75° C. for about 20 min, and slow cooling them to about 24° C. or less, under conditions effective to anneal the single-stranded DNA regions that were generated during (a); and
  (c) incubating the cooled DNA molecules in (b) with Taq DNA polymerase and Taq DNA ligase at about 45° C., in the presence of added dNTPs, under conditions effective to fill in the gaps and seal the nicks, wherein about 6%-8.5% glycerol or 0.25 M-1.50 M D-Sorbitol is present throughout the joining procedure.

Another aspect of the invention is an in vitro method, using isolated (for example, substantially purified) proteins, for joining at least two dsDNA molecules of interest, each of about 120 bases to about 6 kilobases (kb), wherein the distal region of the first DNA molecule and the proximal region of the second DNA molecule of each pair share a unique region of sequence identity, comprising
  (a) incubating approximately equimolar amounts of the DNA molecules with: T4 DNA polymerase; and a ligase that is compatible with the polymerase, at about 37° C., in the absence of added dNTPs, under conditions effective to chew-back at least the regions of sequence identity in each molecule, thereby forming single-stranded overhanging ends of sufficient length to hybridize specifically to overhangs having the complement of the shared region of sequence identity, and to allow hybridization of the single-stranded overhangs, thereby forming gapped molecules; and
  (b) incubating the gapped DNA molecules of (a) with a sufficient amount of dNTPs, under conditions effective to allow filling in of the gaps, generation of nicks, and sealing of the nicks,
wherein the method is carried out in a single vessel.

Another aspect of the invention is an isothermal method similar to the preceding method, except the ligase is not present during the initial chew-back/annealing reaction, but instead is added with the dNTPs during the repair reaction.

The methods of the invention may be used to join at least about 4 (for example, at least about 6 or 8) double-stranded DNA molecules, wherein for each pair of molecules to be joined, the distal region of one DNA molecule comprises a region of sequence homology to the proximal region of the other DNA molecule, and each set of distal and proximal regions of homology is unique for each pair of DNA molecules to be joined.

In methods of the invention, the DNA molecules to be joined can be at least about 120 bases (for example, at least about 120 bases, about 200 bases, about 400 bases or more).

In methods of the invention, the DNA molecules to be joined can be at least about 5 kb (for example, at least about 25 kb, 140 kb, 500 kb, or $1 \times 10^6$ bp).

Methods of the invention can be carried out in a single vessel (tube, vial, etc.). For example, in one embodiment, the chew-back and annealing steps are carried out in a solution that comprises about 0.2 M Tris-Cl, pH 7.5 and about 6%-8.5% glycerol or about 0.25 M-1.50 M D-Sorbitol; and when the chew-back/annealing reactions are complete, the reaction mixture is diluted 1:4; more glycerol is added to a final concentration of about 6%-8.5% (or additional D-Sorbitol to a final concentration of 0.25 M-1.50 M); and the repair reaction is allowed to proceed.

The DNA molecules of interest can comprise a vector DNA molecule, and the joined DNAs of interest can thus be cloned into the vector.

In methods of the invention, one or more (for example, all) of the plurality of DNA molecules are generated synthetically, or are copies of DNA that has been generated synthetically. The DNA molecules may be adjacent sequences of a gene or genome of interest. In one embodiment, the DNA molecules are synthesized so as to comprise overlapping regions of sequence identity at their ends, and the DNA molecules are joined to form part or all of a synthetic gene or genome.

A method of the invention can further comprise repeating the method to join a second set of two or more DNA molecules of interest to one another, and then repeating the method again to join the first and second set DNA molecules of interest.

Another aspect of the invention is an in vitro method for joining two or more double stranded DNA molecules of interest, as discussed above, further wherein each of the DNA molecules of interest comprises, at the free end of the region of sequence identity, a restriction enzyme cleavage site (such as a Not I site) that is not present elsewhere in the DNA molecules of interest; the DNA molecules of interest are cleaved with the restriction enzyme; and during the repair steps, the restriction enzyme cleavage site is removed from the joined molecules.

Another aspect of the invention is an in vitro method, using isolated (for example, substantially purified) proteins, for joining two or more single-stranded (ss) DNA molecules of interest, wherein the distal region of the first DNA molecule and the proximal region of the second DNA molecule of each pair share a region of sequence identity, comprising
  (a) incubating the single-stranded DNA molecules under conditions effective to achieve specific annealing of the regions of sequence identity, thereby forming molecules with single stranded gaps; and
  (b) treating the gapped molecules in (a) under conditions effective to fill in the gaps and to seal the nicks thus formed,
wherein the region of sequence identity comprises at least 20 (for example, at least about 40) non-palindromic nucleotides (nt) and, optionally,
wherein a chaperone agent (such as glycerol, for example, 6%-8.5% glycerol, or D-Sorbitol, for example, 0.25 M-1.50 M D-Sorbitol) is present during steps (a) and (b); and/or the molecules in step (b) are treated with Taq ligase; and/or a protein that enhances annealing of single-stranded DNAs (such as, for example, RecA, a single-stranded binding protein, or T4 gene 32 protein) is present during steps (a) and (b).

Any of a variety of 3→5' or 5→3' or double-strand specific exodeoxyribonucleases may be used to chew-back the ends of DNA molecules in the methods of the invention. The term "3' exonuclease" is sometimes used herein to refer to a 3→5' exodeoxyribonuclease. Digestion with a 3' exonuclease produces 5' single-stranded overhangs in the DNA molecules. The term "5' exonuclease" is sometimes used herein to refer to a 5→3' exodeoxyribonuclease. Digestion with a 5' exonuclease produces 3' single-stranded overhangs in the DNA molecules. Methods for preparing and using exonucleases and other enzymes employed in methods of the invention are conventional; and many are available from commercial sources, such as USB Corporation, 26111 Miles Road, Cleveland, Ohio 44128, or New England Biolabs, Inc. (NEB), 240 County Road, Ipswich, Mass. 01938-2723.

One aspect of the invention is an in vitro joining method as above, wherein the enzyme in the first step exhibits a 5→3' exonuclease activity. Examples of enzymes having a suitable 5' exonuclease activity include, for example, phage T5 exonuclease, phage T7 exonuclease (phage T7 gene 6 product), phage lambda exonuclease, Redα of lambda phage, or RecE of Rac prophage.

When a 5' exonuclease is used, single-stranded overhangs are generated at the 5' end of DNA molecules that cannot be repaired, unless, for example, the molecules can form a circle, or other procedures are introduced to block exonuclease digestion of these 5' termini. Non-strand displacing DNA polymerases used in methods of the invention must elongate in the 5' direction from a primer molecule. Because no primer is available to be extended in the 5'-located gap in a DNA molecule that has been chewed back with a 5' exonuclease, the gap cannot be filled in by a polymerase. In one embodiment of the invention, the 5' ends of the terminal DNA fragments that are to be joined are blocked so that 5' exonuclease cannot digest them. The blocking agent is preferably reversible, so that the joined DNA molecule can eventually be joined into a vector. Suitable blocking agents will be evident to the skilled worker. These include, for example, phosphorothioate bonds, 5' spacer molecules, locked nucleic acid (LNA) etc. In another embodiment of the invention, the fragments are selected (designed) so that the two terminal fragments join to one another to form a circle. In another embodiment, the joined fragments are designed so that they become integrated into a vector that is also present in the reaction mixture.

In one embodiment of the invention, the enzyme in the first step exhibits a 3'-5' exonuclease activity (sometimes referred to herein as a 3' exonuclease activity). Any of a variety of enzymes can be used in this step. For example, the enzyme can be a 3' exonuclease, such as exonuclease III. In another embodiment, the enzyme is a DNA polymerase that, when incubated under effective conditions, expresses a net 3' exonuclease activity. Suitable conditions include incubation in the absence of added dNTPs. (There may be a small amount of residual dNTPs in a reaction mixture, but these are not in a sufficient amount to allow the polymerase activity of the enzyme to cancel out the exonuclease activity.) Among the suitable DNA polymerases that can be used (in the absence of added dNTPs) are, for example, T4 DNA polymerase, T7 DNA polymerase, E. coli DNA polymerase I, Klenow DNA polymerase, Phi 29 DNA polymerase, Pfu polymerase, Phusion™ High-Fidelity polymerase, Vent$_R$, Deep Vent$_R$, or 9° N$_m$ DNA polymerase. Preferably, the enzyme is T4 DNA polymerase or T7 DNA polymerase that has very similar properties with respect to 3' exonuclease activity.

Advantages of T4 DNA polymerase include: (a) it provides excellent synchronicity in exposing single-stranded DNA; (b) the reactions can be easily controlled to expose different amounts of single-stranded DNA; (c) the exonuclease activity of T4 DNA polymerase does not degrade DNA as rapidly as other exonucleases and therefore, does not require large amounts of input DNA; and (d), like all the mesophilic DNA polymerases discussed herein, it can be heat-inactivated.

Under suitable conditions that will be evident to the skilled worker, T4 DNA polymerase can chew-back DNA molecules having blunt ends, or 5' or 3' single-stranded overhangs.

Thermophilic polymerases (for example, Vent) have the advantage that, because they operate at high temperatures, secondary structures in the DNA template may be removed at the high temperature, so the polymerase molecules are not slowed down by secondary structure. This permits more rapid exonuclease digestion than is accomplished with enzymes that function at lower temperatures, and allows for the digestion of longer overhangs. However, because of the stability of these enzymes at high temperatures, it is difficult to inactivate them by heat, and a more cumbersome procedure, such as the PCI procedure discussed below, must generally be used.

Exonuclease digestion is carried out under conditions that are effective to chew-back a sufficient number of nucleotides to allow for specific annealing of the exposed single-stranded regions of homology. In general, at least the entire region of overlap is chewed back, leaving overhangs that comprise the region of overlap. Such an exonuclease digestion is illustrated in FIG. 1. In other embodiments, for example, when the region of overlap is very long, it may only be necessary to chew-back a portion of the region (for example, more than half of the region), provided that the single-stranded overhangs thus generated are of sufficient length and base content to anneal specifically under the conditions of the reaction. By "annealing specifically" is meant herein that a particular pair of single-stranded overhangs will anneal preferentially (or only) to one another, rather than to other single-stranded overhangs that are present in the reaction mixture. By "preferentially" is meant that at least about 95% of the overhangs will anneal to the paired overhang. A skilled worker can readily determine the optimal length for achieving specific annealing of a sequence of interest under a given set of reaction conditions. Generally, the homologous regions of overlap (the single-stranded overhangs or their complements) contain identical sequences. However, partially identical sequences may be used, provided that the single-stranded overhangs can anneal specifically under the conditions of the reactions.

A variety of buffers, salts, and energy sources can be used in the chew-back reactions. Some exemplary reaction components are disclosed in the Examples. The digestion reaction is carried out for a period of time that is a function of the size of the overlapping region and the temperature of the reaction. For example, using a T4 DNA polymerase, a 5-min reaction at about 37° C. is sufficient to chew-back overlaps of about 40-80 bases, and a 15-min reaction at about 37° C. is sufficient to chew-back overlaps greater than about 300 bases. For Vent/Deep Vent polymerase, an incubation time of about 30 sec at 65° C. is sufficient to chew-back overlaps of about 40 bases, and about 90 sec at 65° C. to chew-back overlaps of about 300 bases. In general, the amount of exonuclease activity used is between about 0.1 and about 70 U/ml. (All enzyme units used herein are units as defined by NEB.)

The exonuclease reaction can be terminated by any of a variety of procedures and, at the same time or subsequently, the reaction mixture can be treated to facilitate the annealing of the single-stranded overhangs. In one embodiment, the exonuclease-digested mixture of the first step is terminated with a conventional PCI procedure (as used herein, a "PCI procedure" refers to extraction with phenol/chloroform/isoamyl alcohol, followed by precipitation with ethanol and drying of the pellet by evaporation, such as in a Speed-Vac). "Cleaning up" the DNA mixture in this manner terminates the exonuclease digestion and enhances the efficiency of annealing of the single-stranded overhangs. In fact, in some embodiments, nearly all or all of the annealing of the single-stranded overhangs may occur during the PCI procedure.

In another embodiment of the invention, following the chew-back reaction, the mixture is incubated at an effective temperature, for example, at 75° C. plus or minus about 5° C., for an effective period of time. The heating step is effective to initiate the annealing reaction and, in some cases, to inactivate the enzyme having an exonuclease activity. In one embodiment, in that a clean-up procedure, such as a PCI procedure, is not required, this heating step is carried out in the presence of a suitable amount of a chaperone agent. A variety of suitable chaperone agents will be evident to the skilled worker. These include a variety of well-known small molecules, such as glycerol, D-mannitol, D-theritol, meso-erythritol, D-adonitol, L-arabitol, D-sorbitol, xylitol, trehalose, maltose, sucrose, glycine, betaine, taurine, β-casein, arginine, proline, sarcosine, sorbitol, myo-inositol and trimethylamine or the like. Much of the discussion in this application is directed to glycerol, Betaine or D-Sorbitol. However, the discussion is meant also to apply to other suitable chaperone agents. A skilled worker will recognize how to implement routine changes in the method in order to accommodate the use of other chaperone agents.

In general, when glycerol is used as a chaperone agent, a concentration of about 6%-8.5% (weight/volume) is optimal. However, the amount of glycerol can range from about 4 to about 21%. In a preferred embodiment of the invention, the glycerol is added at the beginning of the recombination reaction (during the exonuclease digestion).

In general, when D-Sorbitol is used as a chaperon agent, a concentration of about 1.00 M is optimal. However, the amount of D-Sorbitol can range from about 0.25 M to about 1.5 M.

Therefore, the exonuclease digestion, heating and slow cooling steps can all be carried out in a single vessel (for example, tube or vial), for example in a thermocycler, without having to open the vessel to add the glycerol for the annealing step. In a preferred embodiment, a chaperone agent such as glycerol (for example, about 6%-8.5% glycerol) is also present during the repair reaction that it is believed to enhance ligation. In another preferred embodiment, a chaperone agent such as D-Sorbitol (for example, about 0.25 M-1.50 M D-Sorbitol) is also present during the repair reaction that it is believed to enhance ligation. Surprisingly, the present inventors have found that if a chaperone agent (for examples, glycerol, Betaine or D-Sorbitol, among others) is present during all of the steps of the recombination reaction, the total amount of recombination is increased dramatically. See the accompanying examples.

In some embodiments of the invention, for example, when the exonuclease activity is provided by T4 DNA polymerase, it may not be necessary to inactivate the exonuclease activity prior to the repair reaction. For example, following the chew-back and annealing reactions, (a) the reaction mixture can be kept at about 4° C. (or, when the reaction mixture is only to be held for about 2-3 hrs, at as high as about 22° C.-24° C.) before the repair reaction is begun, and/or (b) dNTPs can be added immediately. These procedures inhibit the 3'5' exonuclease activity of the T4 DNA polymerase.

Annealing of the single-stranded overhangs may be performed by first incubating the DNA molecules at a suitable temperature (for example, 75° C. plus or minus about 5° C.). This heating procedure allows single-stranded overhangs that have annealed, either correctly or incorrectly, to come apart. Also, without wishing to be bound by any particular mechanism, it is suggested that heating of the molecules may "un-kink" the single-stranded regions and render them more amenable to hybridizing, and/or to initiate the hybridization. Suitable lengths of times for incubating the DNA molecules will be evident to the skilled worker, for example, at 75° C. plus or minus about 5° C. for about 15-30 min, preferably for about 20 min. The term "about," as used herein, refers to plus or minus 20%. Thus, "about" 20 min includes 16-24 min. "About" also refers to plus or minus 20% when referring to lengths of nucleic acids, temperatures, etc. The end points of ranges, as used herein, are included in the range. Following this heating step, the mixture of DNA molecules is slowly cooled, at a suitable rate, for a suitable amount of time, in a suitable buffer, to allow the single-stranded overhangs to anneal to their specific partners. Generally, "slow cooling" is accomplished at about 6° C./min. Typical slow cooling regimens are shown in the Examples. In general, the reaction mixtures are slowly cooled to room temp (for example, about 22° C. to about 24° C.). However, the reaction mixes may be cooled to about 4° C. to facilitate the storage of the reactions until a subsequent step is performed.

When selecting a temperature for incubating (heating) the DNA molecules, the optimal annealing temperature is a function of the melting temperature of the overlap in question. If more than two DNA molecules are to be joined, an investigator should take into account the likelihood of there being multiple temperatures of annealing. To simplify this step, rather than calculating the Tm's for each overlapping sequence, it is preferable, and simpler, to start at the most stringent Tm expected (generally about 75° C.) and to slow cool to about 22° C. This should cover all possible Tm's of a wide variety of possible overlaps. If desired, one can slow cool only to the Tm of the smallest value, rather than cooling down to 22° C. For example, if the smallest Tm is 50° C., it is only necessary to slow cool to 50° C. Of course, cooling to a lower temperature can be used if it is desirable to store the reaction until a subsequent reaction step is performed. The slow cooling step allows one to anneal a variety of DNA molecules, having overlaps with different $T_m$'s, in a single vessel.

Many embodiments of the invention can be carried out in a single vessel (for example, tube or vial). This can be accomplished, for example, in embodiments in that the exonuclease activity is terminated with a heating step. In such embodiments, a PCI "clean-up" procedure that requires transfer of solution to a second vessel, is not required. Furthermore, the inventors have identified a buffer system (buffers and other reaction components) that, although it may not be optimal for each of the enzymes used, allows each of the enzymes to be sufficiently active to carry out a method of the invention. Thus, it is not necessary to change buffers between steps by transferring the reagents to a new tube. This buffer system is discussed in more detail below.

Following the annealing steps, the single-stranded gaps left by the exonuclease are filled in with a suitable DNA polymerase (sometimes referred to herein as a "polymerase") and the nicks thus formed are sealed with a ligase that is compatible with the DNA polymerase (see FIG. 1). The type of DNA polymerase used is a function of, among other factors, whether the 5' ends of the DNA molecules to be repaired are phosphorylated. In general, between about 10 and about 130 (for example, between about 30 and about 50) U/ml (unit defined by NEB) of DNA polymerase are used in each reaction.

Generally, a DNA polymerase used for the repair step of a method of the invention is a non-strand-displacing DNA polymerase. The enzyme may or may not have a nick-translating activity. A "non strand-displacing DNA polymerase," as used herein, is a DNA polymerase that terminates synthesis of DNA when it encounters DNA strands that lie in its path as it proceeds to copy a dsDNA molecule, or that degrades the encountered DNA strands as it proceeds while concurrently filling in the gap thus created, thereby generating a "moving nick" (nick translation).

In some embodiments of the invention, the DNA polymerase has nick-translation activity. In order for a first DNA molecule to be ligated to the 3'-OH group of another DNA molecule, the first DNA molecule must have a 5' phosphorylated end. A DNA polymerase that has a nick-translation activity creates 5'-ends that are phosphorylated and thus are able to be ligated. Therefore, polymerases with nick-translating activity can be used in methods of the invention with DNA molecules that either have or do not have 5' phosphorylated ends. Taq polymerase or E. coli DNA polymerase holoenzyme are among the suitable DNA polymerases of this type. An advantage of using a polymerase with a nick-translating activity for this step is that it is not necessary to phosphorylate the 5' end of the DNA molecule, thus saving the time and cost of phosphorylating the molecules. Furthermore, such an enzyme can be used to remove unwanted restriction enzyme recognition sites via its nick-translation activity.

In another embodiment, the DNA polymerase does not have a nick translating activity. Such a polymerase is effective only in cases in that the 5' ends are phosphorylated. T4 DNA polymerase, T7 DNA polymerase, Phusion™ polymerase, and Pfu polymerase (when used below about 68° C.) are among the suitable DNA polymerases of this type. If the DNA molecules to be joined are not phosphorylated (for example, are prepared by PCR amplification), the following procedures can be used to allow DNA polymerases lacking nick translation activity be used in the repair reaction: (a) generate the DNA molecules to be joined by PCR, by using PCR primers that have been phosphorylated prior to the PCR, or (b) phosphorylate the 5'-ends using T4 polynucleotide kinase and ATP during the chew-back reaction.

Reaction components (such as salts, buffers, a suitable energy source (such as ATP or NAD), pH of the reaction mixture, etc.) can be optimized for each of the steps of the method. However, to reduce the number of manipulations and to avoid having to change buffers for the exonuclease, annealing and repair reactions, it is preferable to carry out the entire recombination procedure under essentially the same reaction conditions. In some embodiments, the buffers etc. are not optimal for any of the reactions, but can serve as a compromise that is effective for the entire set of reactions. Some exemplary reaction conditions are presented in the Examples. For example, in one embodiment, the chew-back and annealing reactions are carried out in a solution that comprises about 0.2 M Tris-Cl, pH 7.5 and a suitable amount of a chaperone agent, such as about 6%-8.5% glycerol or 0.25 M-1.50 M D-Sorbitol (as well as other components, such as BSA, about 10 mM $MgCl_2$, and DTT). Following completion of the chew-back and annealing reactions, the reaction mixture is diluted 1:4 that reduces the concentration of Tris to 0.05 M, and a suitable amount of a chaperone agent, such as glycerol is added to a final concentration of about 6%-8.5%. Other chaperone agents can also be used, such as D-Sorbitol to a final concentration of about 0.25 M-1.50 M. Other ingredients may also be added to the repair mixture, for example, dNTPs, $MgCl_2$ to a final concentration of about 10 mM, DTT, an energy source for the ligase (such as NAD or ATP), and the enzymes for the repair reaction (polymerase and ligase). Surprisingly, the inventors have found that the use of a high concentration of Tris at pH 7.5 in the chew-back/annealing reaction, and/or the presence of a suitable amount of a chaperone agent, such as about 6%-8.5% glycerol or 0.25 M-1.50 M D-Sorbitol, in all steps of the recombination reaction provide superior overall results as compared to conditions recommended by the manufacturers of the enzymes used in the procedure.

The nicks generated by the gap-filling reaction can be sealed with any of a variety of suitable DNA ligases (sometimes referred to herein as "ligases"). Among the suitable ligases are, for example, phage T4 DNA ligase, *E. coli* DNA ligase, Taq DNA ligase, Ampligase, or the phage T7 gene 1.3 product. In general, about ⅒ volume of ligase is added. Thus, the final concentration of ligase in the reaction mixture is generally about 40 U/μl of T4 ligase, about 4 U/μl of Taq ligase, or about 1 U/μl of *E. coli* DNA ligase. Preferably, the repair reactions are carried out with a polymerase and a ligase that are compatible, and can be used simultaneously. that is, the two enzymes can be incubated under conditions that are suitable for both enzymes. Typical examples include: repair with Taq DNA polymerase, Taq DNA ligase, and an energy source, such as NAD, at about 45° C. (for example, for about 15 min), in a reaction mixture such as that described in Example IX; or incubation with *E. coli* DNA polymerase I and T4 DNA ligase, and an energy source, such as ATP, at about 37° C. (for example, for about 15 min), in a reaction mixture such as that described in Example VIII. Other combinations will be evident to the skilled worker. For example, because Taq polymerase exhibits some activity at 37° C., it may be paired with a ligase that functions at 37° C.

The reaction conditions are selected so that the ligation activity is greater than the polymerase activity. For example, the inventors have found, surprisingly that when using Taq DNA polymerase and Taq DNA ligase, it is optimal to incubate the reaction at about 45° C. (rather than 65° C. or 75° C. that are optimal for the ligase and the polymerase, respectively); incubation at 45° C. results in a balance of the enzymatic activities in favor of the ligation reaction. The inventors have also found that, when setting up such a repair reaction, it is preferable to place the reaction components at 4° C. (for example, on ice). If this is not done, and the reaction mixture is allowed to sit at room temperature for as short a time as one or two min, the Taq polymerase will begin filling in the gaps and disrupting the complex before the Taq ligase has had a chance to function. If the reaction is performed in a thermocycler, it may be convenient to slow cool the chew-back/annealing reaction to 4° C., then to add cold (for example, 4° C.) repair reaction. The thermal cycler can then be set at about 45° C. once all the components have been added.

In one embodiment, substantially all of the nicks (or all of the nicks) are sealed during the reaction procedure. However, in one embodiment, joined DNA that still comprises some nicks is transformed into a bacterium, such as *E. coli*, and the bacterial machinery seals the nicks.

In one embodiment of the invention, the entire procedure is carried out as a "one-step" reaction (in a single tube that does not have to opened during the entire recombination procedure, in a thermocycler apparatus). In one such procedure, a mixture of the DNAs to be joined is incubated at 37° C. with exonuclease III; Taq DNA polymerase; Taq DNA ligase; dNTPs and a buffer compatible with all of these enzymatic activities. Because the Taq enzymes are not very active at 37° C., the exonuclease III prevails, and chew-back and annealing reactions occur during this incubation. The temperature is then raised to 55° C. The exonuclease III is inactive at this temperature, so the repair reactions can occur.

Methods of the invention are generally carried out in vitro. That is, all of the protein components are isolated and/or substantially purified. The in vitro recombination reactions are not carried out in a living cell or with a crude cell extract; the reactions are carried out in a cell-free environment.

In methods of the invention, a plurality of DNA molecules are contacted with the enzymes under conditions effective to join the DNA molecules to form a substantially intact (preferably having no nicks) double-stranded DNA molecule (for example, in that a single copy of the region of sequence identity is retained).

DNA molecules of any length can be joined by methods of the invention. The minimum size for joining molecules with a 40 bp overlap is about 80 bp. For molecules with a 200 bp overlap, the minimum size is about 400 bp. Theoretically, there should be no maximum size of DNA molecules that can be joined (although very large molecules would be more fragile than smaller ones, and thus subject to possible breakage). For example, cassettes having about 100 bp to about 300 kb (or greater) can be joined.

From two to an essentially unlimited upper level of DNA molecules can be joined. In general, at least about 10 fragments can be joined. The number of fragments that can be joined depends, in part, on the length of the overlaps and the lengths of the fragments. For example, with fragments having overhangs of about 150 to about 200 bp (for example, fragments of about 3 kb, or larger or smaller), the number of fragments that can be joined is substantially unlimited. The number of fragments that can be joined in one reaction also depends, in part, on the efficiency of the joining process. If the efficiency of joining is 100%, then an infinite number of DNA molecules could theoretically be joined (provided that an approximately equal number of molecules of each substrate is present in the reaction). With lower efficiencies (for example, about 75-90% joining of each pair of two molecules), two to about 250 DNA molecules can be joined. Methods of the invention work well with a wide range of substrate DNA (for example, about 10 to about 1000 ng of each substrate in a reaction mixture.)

In some embodiments of the invention, the joined DNA molecules form a circle and/or become ligated into a vector to form a circle. The lower size limit for a dsDNA to circularize is about 200 base pairs. Therefore, the total length of the joined fragments (including, in some cases, the length of the vector) is preferably at least about 200 bp in length. There is no practical upper size limit, and joined DNAs of a few hundred kilobase pairs, or larger, can be generated by a method of the invention. The joined DNAs can take the form of either a circle or a linear molecule.

More particularly, the number of DNA molecules or cassettes that may be joined in vitro to produce an end product, in one or several assembly stages according to the invention, may be at least or no greater than about 2, 3, 4, 6, 8, 10, 15, 20, 25, 50, 100, 200, 500, 1000, 5000, or 10,000 DNA molecules, for example in the range of about 4 to about 100 molecules. The number of assembly stages may be about 2, 4, 6, 8, 10, or more. The number of molecules assembled in a single stage may be in the range of about 2 to about 10 molecules. The methods of the invention may be used to join together DNA molecules or cassettes each of which has a starting size of at least or no greater than about 80 bases, 120 bases, 200 bases, 400 bases, 500 bases, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of about 120 bases to about 500 kb. The DNA end products of the inventive methods may be at least about 160 bases, 240 bases, 400 bases, 1 kb, 3 kb, 5 kb, 6 kb, 10 kb, 18 kb, 20 kb, 25 kb, 32 kb, 50 kb, 65 kb, 75 kb, 150 kb, 300 kb, 500 kb, 600 kb, 1 Mb, or larger, for example in the range of 30 kb to 1 Mb.

When joining a mixture of DNA molecules, it is preferable that the DNAs be present in approximately equimolar amounts. If the number of DNA molecules is not balanced, the result would be a termination of assembled species. For example, consider an example in that 8 DNA molecules are to be assembled (numbered 1-8). If, for example, there was an excess of molecule number 4, the majority of assembled molecules would be 1-4 and 4-8. Assuming only a few hundred bases is being chewed back in the reaction, there would be no sequence homology between the distal region of 1-4 and the proximal region of 4-8, thereby decreasing the amount of 1-8.

In methods of the invention, the distal region of one of a pair of dsDNA molecules to be joined shares a region of sequence homology (for example, sequence identity) with the proximal region of the other dsDNA molecule. The term "distal" as used herein refers to the 3' end of a first DNA molecule of a pair to be joined (the 5'-most DNA molecule), and the term "proximal" refers to the 5' end of the second DNA molecule of the pair. The regions of homology are sometimes referred to herein as "overlaps" or "regions of overlap." FIG. 1 shows a schematic representation of the distal and proximal regions of DNA molecules to be joined. A "region of sequence homology (identity)", as used herein, refers to both strands of the double-stranded DNA molecule. Thus, one strand from this region can hybridize specifically to its complementary strand, for example, when the complementary regions are present in single-stranded overhangs from the distal and proximal regions of the two molecules to be joined.

The region of sequence identity should be sufficiently long to allow specific recombination to occur. That is, it should be long enough so that the region of overlap at the ends of two DNA molecules to be joined is unique to those DNA molecules, and no other DNA molecules will anneal to those two DNA molecules during the recombination reaction. The length can vary from a minimum of about 10 base pairs (bp) to about 300 bp or more. For relatively short overlaps (for example, up to about 40 or 60 nt), it is preferable that the sequences be non-palindromic. In general, it is preferable that the length of the overlap is less than or equal to about ½ the size of the fragment to be combined, but not less than about 10 bp and not more that about 1000 bp. For the joining of 2 or 3 fragments, about 20-30 non-palindromic bp overlap may be sufficient. For more than 10 fragments, a preferred overlap is about 80 bp to about 300 bp. In one embodiment, the region of sequence identity is of a length that allows it to be generated readily by synthetic methods, for example, about 40 bp (for example, about 32 to about 48 bp). The overlaps may be, for example, about 10, 20, 30, 40, 50, 60, 70, 80, 90, 100, 150, 200, 250, 300, 350, 400, 450, 500, 550, 600, 650, 700, 750, 800, 850, 900, 950 or 1,000 nt in length.

In a preferred embodiment, when a plurality of DNA molecules are to be joined, for each pair of DNA molecules to be joined, the distal region of one of the DNA molecules of the pair is designed to share a region of sequence identity with the proximal region of the other DNA molecule of the pair, and the distal and proximal regions of sequence identity for each pair of DNA molecules are designed to be unique (to be different from the regions of sequence identity of the other pairs of DNA molecules). When the overlapping regions of identity are designed in this manner, the orientation and order of the DNA molecules in the joined molecule can be predetermined. A number of DNA molecules (for example, 4 or 6 molecules) can thus be incubated together in a single reaction mixture (in a single vessel or container) in a method of the invention, and be joined into a longer DNA molecule in that the individual DNAs are arranged in any desired order and orientation.

The regions of sequence identity present in the proximal and distal regions of the DNAs to be joined can be generated by any of a variety of methods.

For example, in one embodiment of the invention, synthetically prepared, overlapping fragments of a gene or genome of interest (for example, about 120 bases to about 6 kb in length, or longer or shorter) are optionally amplified (for example, by PCR, or by MDA such as a rolling circle mechanism) and are joined by a method of the invention in the order and orientation in that they are located in the gene or genome. In this method, the first DNA fragment (for example, in the 5' most portion of the gene or genome) is synthesized so that the region at its 3' end (the distal end) contains a sequence (for example, about 40 bp) that is identical to the sequence at the 5' end (the proximal end) of the DNA fragment to that it is to be joined. The second DNA fragment, in turn, is synthesized so that it has, at its distal end, a sequence that is identical to the sequence at the proximal end of the third DNA fragment, and so on. In another embodiment, synthetically prepared fragments of a gene or genome of interest are inserted into a vector, propagated in *E. coli* to make more of the synthetically prepared fragment, then released from the vector, optionally amplified further by PCR, MDA or RCA, and joined by a method of the invention in the order and orientation in that they are located in the gene or genome. These procedures allow the preparation of a synthetic gene or genome.

In another embodiment of the invention, two fragments to be joined are generated by restriction enzyme digestion, such that the fragments overlap one another, for example, by about 20-about 1000 bp. The overlapping regions can then be joined by a method of the invention. Greater numbers of fragments can also be generated by these methods and joined. Combinations of the preceding method and methods using synthetically prepared DNA molecules and/or molecules generated by PCR can be used.

In embodiments of the invention, the regions of identity are introduced by PCR amplification.

In one such method, a fragment of interest is inserted into a vector. For example, a plasmid vector can be linearized with a restriction enzyme, generating a sequence A (for example, having 40 bp) to the left of the restriction enzyme cut and a sequence B (for example, having 40 bp) to the right of the restriction enzyme cut. The fragment to be cloned into the vector is PCR amplified, using PCR primers that will introduce sequence A at the left end of the fragment, and sequence B at the right end of the fragment. The regions of sequence identity (in this example, each having 40 bp) allow the fragment to be joined to the vector in a desired orientation, to form a circular molecule. Alternatively, particularly when it is desirable to avoid errors that might be introduced into an insert during PCR amplification, the vector can be PCR amplified in order to introduce at the ends of a cloning site sequences that overlap sequences at the ends of the insert. The methods described above allow for the directional cloning of any insert of interest, without having to rely on the presence of, or introduction of, restriction enzyme sites on the insert.

In a variation of the preceding method, two or more (for example, three or more) DNA fragments are joined to one another to form a linear molecule. In this variation of the preceding method, regions of sequence identity that are unique to each pair of fragments to be joined are introduced into the fragments by PCR amplification, using suitable primers. For each DNA fragment to be joined to another fragment, a sequence is introduced to the 3' (distal) end of the first fragment that overlaps with the sequence at the 5' (proximal) end of the fragment to that it is to be joined. As in the preceding method, PCR primers are used in that the regions of sequence identity (for example, 40 nt) lie 5' to a PCR primer (for example, having 20 nt). After a suitable number of rounds of PCR amplification, DNA fragments are produced in that defined regions of sequence identity are present at the ends of the fragments. The resulting fragments can then be joined in a predetermined order and orientation by a method of the invention.

If desired, the joined, linear DNA fragments may be circularized, or they may be inserted into a vector to form a circle (simultaneously with the joining of the fragments, or subsequent to that joining). For example, a vector can be present in the joining reaction, so that the joined fragments are introduced into the vector. The efficiency of joining a large number of fragments (for example, 6 or 8 fragments) into a vector by a method of the invention is greater than when using a method that employs compatible restriction enzyme sites. In a typical cloning experiment with restriction enzymes and T4 DNA ligase, probability is not in favor of the researcher getting multiple inserts to ligate into a vector. However, in the assembly methods of the invention, a researcher can join about 6 inserts into a vector with approximately 20-50% efficiency, or greater. Furthermore, since the efficiency is high, there is an increased ratio of recombinants to non-recombinants. The background level of non-recombinants can be reduced further by isolating a pure band by agarose gel electrophoresis (since this method produces a high enough yield to isolate a band on agarose gels) or with a sizing column. A DNA of the desired size (having the correct number of joined DNA molecules) can be isolated and introduced into a vector, for example, using a method of the invention. If the final product is a circle, there is no need to isolate it by agarose gel electrophoresis. Rather, the sample can be treated with an enzyme such as Plasmid-Safe (Epicentre), an ATP-dependent DNAse that selectively hydrolyzes linear dsDNA but not circular dsDNA. If the user's application does not require a pure clone, there may be a sufficient amount of DNA without the need to transform into E. coli and do plasmid preparations.

In one embodiment, joined DNA molecules and/or DNA molecules inserted into vectors are introduced into a host cell, such as a bacterial or eukaryotic cell (for example, by transformation or transfection). Alternatively, the reaction mixture comprising the joined DNA molecules can be introduced into a host cell; only those DNAs that have recombined to form circular molecules can survive in the host cell. In another embodiment, the joined fragments and/or fragments inserted into vectors are used directly, without further passage through a cell, such as a bacterial cell.

Molecular biology methods of the invention can be carried out using conventional procedures. See, for example, discussions in Sambrook, et al. (1989), Molecular Cloning, a Laboratory Manual, Cold Harbor Laboratory Press, Cold Spring Harbor, N.Y.; Ausubel et al. (1995). Current Protocols in Molecular Biology, N.Y., John Wiley & Sons; Davis et al. (1986), Basic Methods in Molecular Biology, Elseveir Sciences Publishing, Inc., New York; Hames et al. (1985), Nucleic Acid Hybridization, IL Press; Dracopoli et al. (current edition) Current Protocols in Human Genetics, John Wiley & Sons, Inc.; and Coligan et al. (current edition) Current Protocols in Protein Science, John Wiley & Sons, Inc.

A variety of uses for the inventive method will be evident to the skilled worker. The inventive method can be substituted for any method in that restriction enzyme digests are used to generate compatible sequences for joining DNA molecules. In one embodiment of the invention, DNA molecules that are too large to be amplified by PCR can be cloned by joining sub-fragments by a method of the invention and then inserting them into a suitable vector. Some pieces of DNA are unstable (and therefore, unclonable) in E. coli, especially those that are high in A+T % content. A method of the invention allows for the assembly of DNA in vitro without the need to be transformed into E. coli. Furthermore, phi29 DNA polymerase can be added to the reaction to amplify the circular DNA. An in vitro recombination system of the invention can be used to recombine any homologous DNAs of interest, for example, to repair double-stranded DNA breaks or gaps, etc. Another application of the method is to introduce a mutation into a DNA. In this method, a mutation is introduced into both the upper and lower strand PCR primers, so the amplified fragments are 100% mutant; then the fragments are joined by the method of the invention.

The disclosed methods can be used to join any nucleic acid molecules of interest. The nucleic acid molecules can come from any source, including a cellular or tissue nucleic acid sample, cloned fragments or subclones thereof, chemically synthesized nucleic acids, genomic nucleic acid samples, cDNAs, nucleic acid molecules obtained from nucleic acid libraries, etc. The DNAs can be radioactively labeled or can comprise binding entities, such as biotinylated nucleotides that can aid in the purification of the joined DNAs. If desired, the DNA molecules to be joined, or primers for adding overlapping regions of sequence identity, can be prepared synthetically. Conventional synthesis techniques include using phosphoroamidite solid-phase chemistry to join nucleotides by phosphodiester linkages. Chemistry for joining nucleotides by phosphorothioate linkages or different linkages, such as methylphosphonate linkages, can also be used. For example, the cyanoethyl phosphoramidite method can be used, employing a Milligen or Beckman System 1 Plus DNA synthesizer (for example, Model 8700 automated synthesizer of Milligen-Biosearch, Burlington, Mass. or ABI Model 380B). Synthetic methods useful for making DNA molecules are also described by Ikuta et al. (1984) Ann Rev. Biochem. 53, 323-356, (phosphotriester and phosphite-triester methods), and Narang et al. (1980) Methods Enzymol. 65, 610-620 (phosphotriester method). DNAs prepared by methods as above are available from commercial sources, such as Integrated DNA Technologies (IDT), Coralville, Iowa.

For certain assembly reactions, such as those using shorter fragments in the range from about 80 bases to about 600 bases, one can rely upon synthetic double-stranded DNA substrates having engineered single-stranded termini for specifying the overhang regions. In these cases, one can dispense with the exonuclease step altogether for generating the single-stranded overhang regions of the double-stranded DNA substrates used for assembling larger products. The assembly reactions can also dispense with the requirement for DNA polymerase having "fill-in" activity prior to ligation depending upon the precise engineering of single-stranded overhangs for contiguous double-stranded DNA fragments. In other words, the disclosed chaperone agents will promote the isothermal assembly of synthetic double-stranded DNA substrates regardless of the means whereby the single-stranded overhangs are generated.

In one embodiment, an in vitro method for joining a first set of double-stranded (ds) DNA molecules is provided. The method includes three steps. The first step includes providing two or more dsDNA molecules to be joined in a reaction mixture. For each pair of dsDNA molecules to be joined, a distal region of a first DNA molecule and a proximal region of a second DNA molecule share a region of sequence homology; a single-stranded overhanging portion is present in each of the dsDNA molecules; and each overhanging portion contains the region of homology or a portion thereof sufficient to specifically anneal to the overhanging portion in the other molecule of the pair. The second step includes incubating the DNA molecules of the first step under conditions whereby they anneal through the regions of homology or portions thereof. The third step includes treating the annealed molecules with an optional, substantially purified polymerase and a substantially purified compatible ligase, under conditions whereby remaining single-stranded gap(s) are filled in by the polymerase and nicks are sealed by the ligase; thereby joining the dsDNA molecules.

A chaperone agent can be present in the reaction mixture during each of second and third steps. The chaperone agent is selected from the group consisting of glycerol, D-mannitol, D-theritol, meso-erythritol, D-adonitol, L-arabitol, D-sorbitol, xylitol, trehalose, maltose, sucrose, glycine, betaine, taurine, β-casein, arginine, proline, sarcosine, sorbitol, myo-inositol and trimethylamine. The chaperone agent is preferably glycerol, wherein the concentration of glycerol in the reaction mixture ranges form about 6% to about 8.5% glycerol. The chaperone agent is most preferably D-Sorbitol, wherein the concentration of D-Sorbitol in the reaction mixture ranges form about 0.25 M to about 1.50 M D-Sorbitol.

The polymerase in third step, if present, is Taq DNA polymerase. In such cases where a Taq DNA polymerase is included, a compatible ligase in the third step is Taq ligase.

The incubating in the second step can be carried out by subjecting the molecules to conditions effective to separate any single-stranded portions that have annealed and followed by slowly cooling the molecules to about 24° C. or less, under conditions effective to allow the single-stranded overhanging portions to anneal.

In some embodiments, at least four dsDNA molecules are joined and each shared region of sequence homology is unique for each pair of DNA molecules joined. In some embodiments, at least eight dsDNA molecules are joined.

In some embodiments, the DNA molecules to be joined are at least about 120 bases in length. In some embodiments, the DNA molecules to be joined are at least about 200 bases in length. In some embodiments, the DNA molecules to be joined are at least about 400 bases in length.

In some embodiments, for at least one pair of dsDNA molecules to be joined, the region of sequence homology comprises at least about 20 non-palindromic nucleotides in length. In some embodiments, for at least one pair of dsDNA molecules to be joined, the region of sequence homology comprises at least about 30 nucleotides in length.

In some embodiments, all the steps are carried out in a single reaction vessel. The method of claim 49, further comprising: (i) joining a second set of dsDNA molecules by performing the first through third steps; and (ii) performing a second stage assembly, comprising the first through third steps anew, wherein the dsDNA molecules provided in the first step comprise a product produced by joining the first set and a product produced by joining the second set.

In some embodiments, method is automated and high-throughput. In some embodiments, the method does not require a PCI clean-up procedure.

In some embodiments, the overhanging portions are generated without the use of a restriction enzyme or a nuclease.

In some embodiments, the dsDNA molecules are joined in a predefined order and orientation.

In some embodiments, the second and third steps are performed in the same reaction mixture, containing the same buffer and reaction components. In some embodiments, the second an third steps are performed in the same reaction vessel and the vessel is not opened between the second and third steps.

In some embodiments, the treating in the third step is performed at between 37° C. and 75° C. Preferably, the treating in third step is performed at 37° C.

Without the claimed subject matter being limited to any particular theory or mode of action, the methods of the invention use chaperone agents to facilitate fragment assembly. Control experiments with supercoiled plasmid in assembly mixes demonstrated that chaperone agents do not enhance plasmid uptake into cells during transformation (see Example 7). The chaperones agents, such as D-Sorbitol, can boost colony counts even when ligase is omitted from the assembly mix (see Example 8), suggesting that assembly mixtures include assembled DNA fragments that are ligated together by bacterial ligases following transformation.

Methods of the invention are amenable to automation and to adaptation to high throughput methods, allowing for the joining of multiple DNA molecules simultaneously by computer-mediated and/or robotic methods that do not require human intervention.

Compositions

Another aspect of the invention is a composition comprising
 (a) an isolated enzyme that, under suitable reaction conditions (such as the absence of added dNTPs) exhibits a 3' or 5' exonuclease activity (for example, T4 DNA polymerase);
 (b) a non strand-displacing DNA polymerase (for example, Taq DNA polymerase);

(c) a DNA ligase that is compatible with the DNA polymerase in (b) (for example, Taq DNA ligase); and optionally, (d) a chaperone agent.

Another aspect of the invention is a composition comprising:

(a) a purified (for example, substantially purified) enzyme that, under suitable reaction conditions exhibits a 3' or 5' exonuclease activity (for example, T4 DNA polymerase, wherein the suitable reaction conditions include the absence of added dNTPs);

(b) a non strand-displacing DNA polymerase (for example, Taq DNA polymerase);

(c) a DNA ligase that is compatible with the DNA polymerase in (b) (for example, Taq DNA ligase); and, optionally, (d) about 0.2 M Tris, pH about 7.5 and/or a suitable amount of a chaperone agent, such as about 6%-8.5% glycerol or 0.25 M-1.50 M D-Sorbitol.

The compositions as above can be present, for example, in a reaction mixture in that a plurality of DNA molecules is being joined by a method of the invention.

DNA used in a method of the invention can be modified in any of a variety of ways, provided that the modified DNA is able to function in the method. A skilled worker can readily determine if a particular modification allows the modified DNA to function (for example, to be recognized by and acted upon by enzymes used in the method).

Another aspect of the invention is an in vitro method to join two or more single-stranded (ss) DNA molecules (for example, ssDNA oligonucleotides) that is similar to the methods discussed above except, because the molecules are already single-stranded, the "chew-back" step is not necessary, that is, the single-stranded molecules are annealed and then repaired. Chemically synthesized oligonucleotides, from about 20 bp to any size that can be synthesized chemically, can be used. For example, 10 ssDNA oligos of about 60 bp, having about 10 bp homology overlap at each end, can be assembled simultaneously into a vector. The assembly of 10 such oligonucleotides results in a DNA molecule of about 500 bp. DNA molecules assembled by this method can, in turn, be joined to one or more other DNA molecules assembled by this (or another) method (for example, as in the preceding case, assemblies of about 500 bp). Repetitions of the method can generate very large molecules of DNA; there is no theoretical limit to the size of a DNA molecule thus generated. The enzymes, buffers, and other reaction conditions described above for the "chew-back/annealing/repair" method can be applied to the present method.

A suitable composition for joining a first set of double-stranded (ds) DNA molecules having pre-engineered overhangs is also provided. The composition includes: (a) an optional non strand-displacing DNA polymerase; (b) a DNA ligase that is compatible with the DNA polymerase in (b); and (c) a chaperone agent. The optional non strand-displacing DNA polymerase, if present, comprises Taq DNA polymerase. The DNA ligase comprises Taq DNA ligase. The chaperone agent is selected from the group consisting of glycerol, D-mannitol, D-theritol, meso-erythritol, D-adonitol, L-arabitol, D-sorbitol, xylitol, trehalose, maltose, sucrose, glycine, betaine, taurine, β-casein, arginine, proline, sarcosine, sorbitol, myo-inositol and trimethylamine. The chaperone agent comprises preferably glycerol or D-Sorbitol.

Kits

Another aspect of the invention is a kit for implementing a method of the invention. The kit can comprise, for example, (a) an isolated (for example, substantially purified) enzyme having a 3' or 5' exonuclease activity (for example, T4 DNA polymerase); (b) an isolated (for example, substantially purified) non strand-displacing DNA polymerase (for example, Taq DNA polymerase); (c) an isolated (for example, substantially purified) ligase that is compatible with the non strand-displacing polymerase (for example, when this DNA polymerase is Taq DNA polymerase, the ligase can be Taq DNA ligase); and, optionally, (d) a solution, or compounds for making a solution that, when combined with the exonuclease and the dsDNA molecules to be joined, comprises about 6%-8.5% glycerol (or alternatively, for example, 0.25 M-1.50 M D-Sorbitol) and/or about 0.2 M Tris, at about pH7.5. In another embodiment, the kit can comprise, for example, (a) a vessel containing isolated (for example, substantially purified) T4 DNA polymerase; a protein that enhances annealing of single-stranded DNAs; and a ligase that is compatible with the polymerase; and, optionally (b) a solution, or compounds for making a solution that, when combined with an aliquot of the protein mixture in (a) and a plurality of suitable DNA molecules containing regions of sequence identity at their termini, is effective to allow chew-back of regions of sequence identity of the DNA molecules, the formation of single-stranded overhangs containing the regions of sequence identity, and hybridization of the single-stranded overhangs, thereby forming gapped molecules; and, optionally (c) a concentrated solution of dNTPs, or reagents for preparing such a solution that, when added in a suitable volume to the solution in (b) that contains gapped molecules, and incubated with that solution under suitable conditions, is effective to allow filling in of the gaps. Each of the components of a kit of the invention can be in separate containers, or two or more components can be in the same container.

Any combination of the materials useful in the disclosed methods can be packaged together as a kit for performing any of the disclosed methods. For example: an enzyme having a 3' or 5' exonuclease activity; a non strand displacing DNA polymerase; a ligase that is compatible with the polymerase; and, optionally, a protein that enhances the annealing of single-stranded DNAs can be packaged individually or in various combinations. Sufficient amounts of these protein reagents for many reactions may be present in a single vial, and aliquots may be removed for individual reactions; or the proteins may be packaged in amounts suitable for a single use. In one embodiment, the polymerase and the ligase are packaged together. In another embodiment, a polymerase (that serves as either an exonuclease or a polymerase, if dNTPs are absent or present, respectively); Taq DNA polymerase; and Taq DNA ligase are packaged together. Other combinations of proteins for implementing methods of the invention will be evident to the skilled worker. If desired, the protein reagents can be packaged in single use form, suitable for carrying out one set of DNA joining reactions. The protein reagents of the kit may be in containers in that they are stable, for example, in lyophilized form or as stabilized liquids. In one embodiment, the proteins are stored as solutions in 50% glycerol.

Optionally, kits of the invention comprise instructions for performing the method. Other optional elements of a kit of the invention include suitable buffers, packaging materials, etc. Reaction components, such as buffers, salts, glycerol or the like that have been optimized for one or more of the enzymatic reactions, can be included, in a concentrated or a dilute form, along with the enzymes or packaged separately from them. For example, a suitable amount of a chaperone agent, such as glycerol at a final concentration of about 6%-8.5%, (or alternatively, for example, 0.25 M-1.50 M D-Sorbitol) or a concentrated solution that can be diluted to this concentration, can be present in a kit of the invention. Also, or alternatively, about 0.2 M Tris pH7.5, or a concentrated solution that can be diluted to this concentration, can be included in the kit.

A kit of the invention may include one or more separately packaged solutions with components that are suitable for methods of the invention. In one embodiment, the kit contains a first solution, suitable for a chew-back/annealing reaction that comprises a suitable amount of a chaperone agent, such as glycerol (or, for example, D-Sorbitol) (that, after the addition of other components of the reaction, will reach a final concentration of about 6%-8.5%), and/or a Tris buffer (that, after the addition of other components of the reaction, will reach a final concentration of about 0.2 M Tris, at about pH 7.5), to that can be added the DNA molecules to be joined and an enzyme having an exonuclease activity (such as T4 DNA polymerase). This first solution can also include other ingredients, such as $MgCl_2$, DTT, BSA, etc. In one embodiment, the kit also contains a second solution, suitable for a repair reaction that comprises a suitable amount of a chaperone agent, such as glycerol (that, after the addition of other components of the reaction, will reach a final concentration of 6%-8.5%) (or alternatively, for example, 0.25 M-1.50 M D-Sorbitol). This solution can also contain water (that, after the addition of other ingredients, including the chewed-back/annealed DNAs and suitable enzymes for a repair reaction, will bring the final concentration of Tris pH 7.5 to 0.05 M), and other ingredients such as $MgCl_2$, DTT, dNTPs, an energy source for ligase (such as NAD or ATP), etc. To this second solution can be added the reaction mixture that contains the chewed-back/annealed DNAs, and the enzymes for a repair reaction (a polymerase and a compatible ligase). For further guidance as to components that can be present in kits, see the reaction mixtures shown in the Examples.

In one embodiment, the kit comprises two vials: the first vial contains a suitable enzyme having exonuclease activity (for example, T4 polymerase), in a solution containing glycerol and other elements required for optimal exonuclease and annealing activity; and the second vial contains a suitable polymerase for the repair reaction (for example, Taq DNA polymerase), a compatible ligase (for example, Taq DNA ligase), in a solution containing glycerol, a suitable amount of dNTPs, and other elements required for optimal repair activity. With such a kit, the DNAs to be joined are mixed with the contents of the first vial and incubated as described for the chew-back and annealing reactions; then the contents of the second vial are added and the mixture is incubated as described for the repair reaction.

In another embodiment, a kit for joining a first set of double-stranded (ds) DNA molecules having pre-engineered overhangs is provided. The kit comprises: (a) an optional isolated non strand-displacing DNA polymerase; (b) an isolated ligase that is compatible with the isolated non strand-displacing polymerase of (a); and (c) a reagent solution comprising a chaperone agent.

The optional isolated non strand-displacing DNA polymerase, if present, can comprise Taq DNA polymerase. isolated ligase comprises Taq DNA ligase.

The chaperone agent is selected from the group consisting of glycerol, D-mannitol, D-theritol, meso-erythritol, D-adonitol, L-arabitol, D-sorbitol, xylitol, trehalose, maltose, sucrose, glycine, betaine, taurine, β-casein, arginine, proline, sarcosine, sorbitol, myo-inositol and trimethylamine. A preferable chaperone agent comprises glycerol. A more preferable chaperone agent comprises D-Sorbitol.

The reagent solution of the kit can comprise a concentrated amount of the chaperone agent sufficient to enhance joining the first set of double-stranded (ds) DNA molecules in a final mixture comprising the first set of double-stranded (ds) DNA molecules and the components of the kit. The concentrated amount of the chaperone agent comprises an amount of glycerol to provide a final concentration from about 6% to about 8.5% in the final mixture comprising the first set of double-stranded (ds) DNA molecules and the components of the kit. In another embodiment, the concentrated amount of the chaperone agent comprises an amount of D-Sorbitol to provide a final concentration from about 0.25 M to about 1.50 M in the final mixture comprising the first set of double-stranded (ds) DNA molecules and the components of the kit. The reagent solution can further comprise a concentrated amount of Tris pH7.5 buffer sufficient to support joining the first set of double-stranded (ds) DNA molecules in a final mixture comprising the first set of double-stranded (ds) DNA molecules and the components of the kit. The kit can further comprise instructions.

EXAMPLES

The present invention is additionally described by reference to the following Examples that are offered by way of illustration and are not intended to limit the invention in any manner. Standard techniques well known in the art or techniques specifically described below can be utilized. The procedures set forth in the following examples summarize the steps necessary for carrying out preferred embodiments of the method.

Example 1: Enhancement of Isothermal Assembly by Replacement of Crowding Agent with the Chaperone Agent Glycerol A range of multiple double stranded DNA fragments (1-5, approximate size of each fragment 420 bp, sequence shown in Table 1) with 30 bp overlapping ends and a plasmid vector (pUC-IDT AMP, 2752 bp) were subjected to isothermal assembly. Briefly, double-stranded DNA fragments having overlapping ends were initially prepared from templates using primer pairs in PCR assays. The 5' ends of primers include ~30 bases of identical sequences for preparing contiguous fragments designed to have overlapping ends by PCR. The plasmid was linearized by restriction digest and reverse amplification PCR. Briefly, the pUC-IDT AMP plasmid was linearized with EcoRV restriction endonuclease (NEB), subjected to cleanup using the QIAquick PCR Purification Kit (Qiagen). Three nanograms of the digested plasmid was amplified using Phusion High-Fidelity PCR Master Mix with HF Buffer (NEB) in a 100 µl PCR reaction with 200 nM each of forward and reverse primers (SEQ ID No 1 and SEQ ID No 2) with the cycling conditions: 98° $C.^{0:30}$ (98° $C.^{0:10}$-70° $C.^{0:10}$-72° $C.^{1:00}$)×35 cycles). The PCR reaction was separated on a 1% agarose gel at 120 volts for 45 minutes and stained with GelRed Nucleic Acid Gel Stain (Biotium). The 2752 bp band was cut from the gel and extracted using the Zymoclean Gel DNA Recovery Kit (Zymo Research), and further purified using Agencourt AMPure XP beads (Beckman Coulter) at a bead:DNA volume ratio of 0.8:1. The fragments were amplified from a single plasmid target (pET-27b+ plasmid containing a 2447 bp insert). Each fragment was amplified from 2 ng of plasmid using Phusion High-Fidelity PCR Master Mix with HF Buffer in a 100 µl reaction with 200 nM each of forward and reverse primers. Some primers contain 30 bp of extra sequence on the 5' end to aid in generating a 30 bp overlap with the pUC-IDT Amp vector or an adjacent fragment for assembly. The sequences used are shown in Table 1. Primer combinations and the resulting fragments are shown in Table 2.

The assembly mixes contained either the crowding agent PEG-8000 (5%) or the chaperone agent glycerol (6%). In a total reaction volume of 20 uL, 35 fmoles (1.75 nM) of linearized vector was combined with 70 femtomoles (3.5 nM) of each fragment, in the 1× assembly mix that yielded a final concentration of each component listed in Table 3. The fragment combinations used and expected insert sizes for the 1 to 5 fragment assemblies are shown in Table 4. The reactions were incubated for 5, 10 or 60 minutes at 50° C. One microliter of the assembled material was transformed into 30 uL of XL-1 Blue supercompetent bacteria, subjected to heat shock (42° C. for 45 seconds), 1 mL of SOC was added, and the transformation was recovered at 37° C. for 1 hour with shaking at 250 rpm. Post recovery 200 uL of the transformation mixture was plated on the agar plates containing the appropriate antibiotic (ampicillin, 100 ug/mL). Control reactions consisted of incubating only 35 fmoles of pUC-IDT AMP vector DNA in the presence of the assembly mix. Resultant colonies were counted and the results are displayed in Table 5. Colonies were chosen at random for the 60 minute reaction time for the mix containing the crowding agent versus the chaperone agent, plasmid DNA isolated and subjected to Sanger sequencing. The assembly process requires generating overhangs with the T5 exonuclease, and subsequent fill in of gaps by a DNA polymerase and sealing of nicks by a DNA ligase. It is possible for mutations to arrive at the junctions between fragments that are assembled and therefore the fidelity of assembly needs to be verified. The sequencing primers used are shown in Table 1 (SEQ ID NOs: 18-23). The regions surrounding the overlaps were examined in detail to determine the fidelity of the assembly reaction. The sequencing results for the 4 fragment assemblies are shown in Table 6. The fidelity of assembly was 34% greater when the chaperone agent Glycerol was used than when the crowding agent (volume excluder) PEG-8000 was included in the assembly mix.

Another benefit of replacing the crowding agent PEG-8000 with the chaperone agent Glycerol is clearly seen when the incubation time is lowered from 60 minutes to 10 or 5 minutes (Table 5). The assembly mixture containing the PEG-8000 performs very poorly at the shortened incubation times, as seen by the reduced number of colonies. Furthermore, increasing the number of fragments in the assembly reaction severely decreases the efficiency of the process under reaction conditions that contain the crowding agent. These results clearly demonstrate the validity and improvement by replacing the crowding agent with a chaperone agent. Furthermore, the enhanced colony yield observed following transformation with assembly mixtures containing a chaperone agent is not due to improved transformation efficiency by the presence of the chaperone agent in the transformation cocktail (not shown).

Figure 2A:
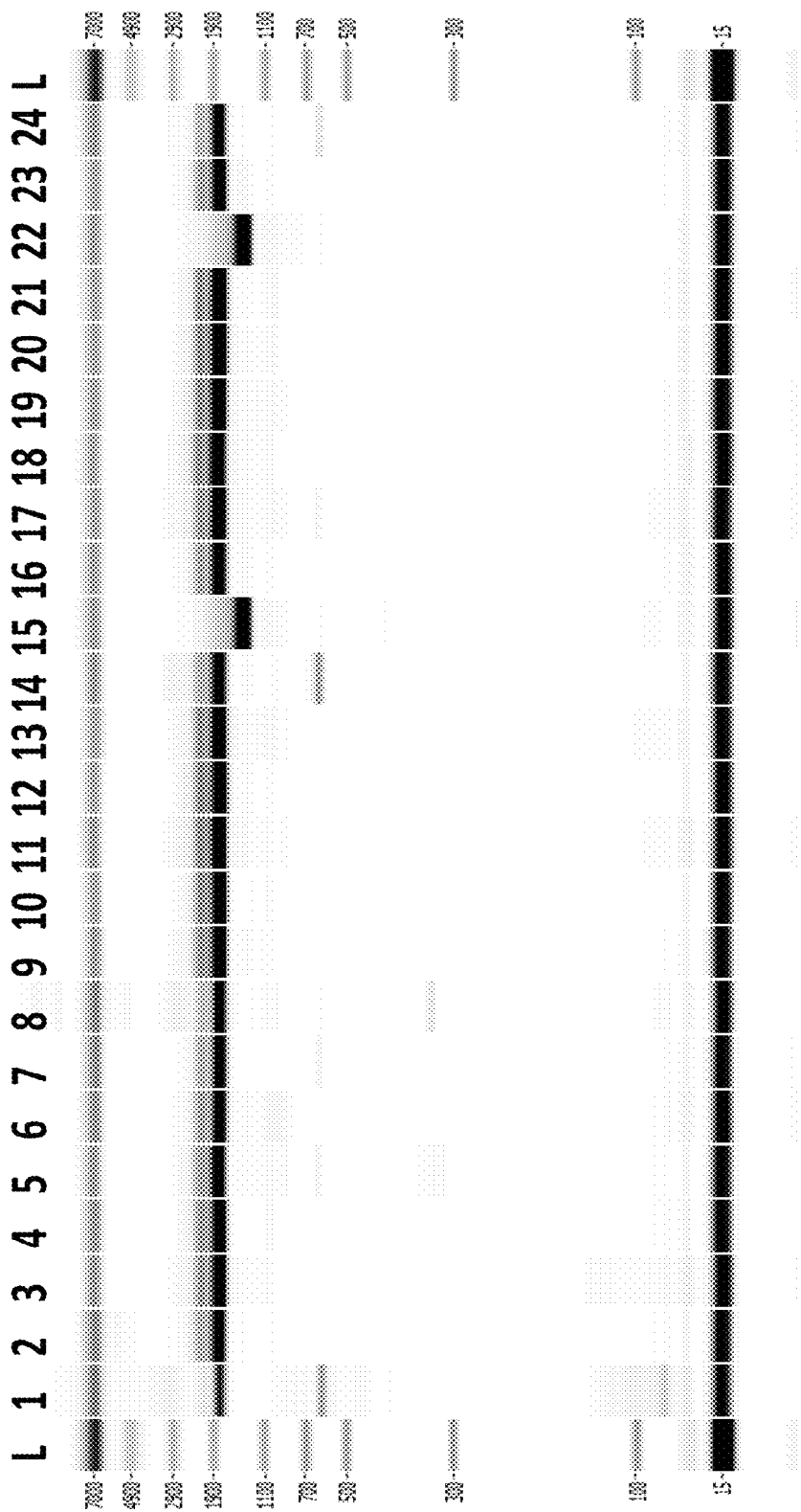
FIG. 2A shows the results from the PCR screen of randomly picked colonies, showing the majority of clones contain the expected full-length insert for exemplary Lab-Chip GX electropherogram results from the 4 fragments plus vector assembly reaction.
Figure 2B:
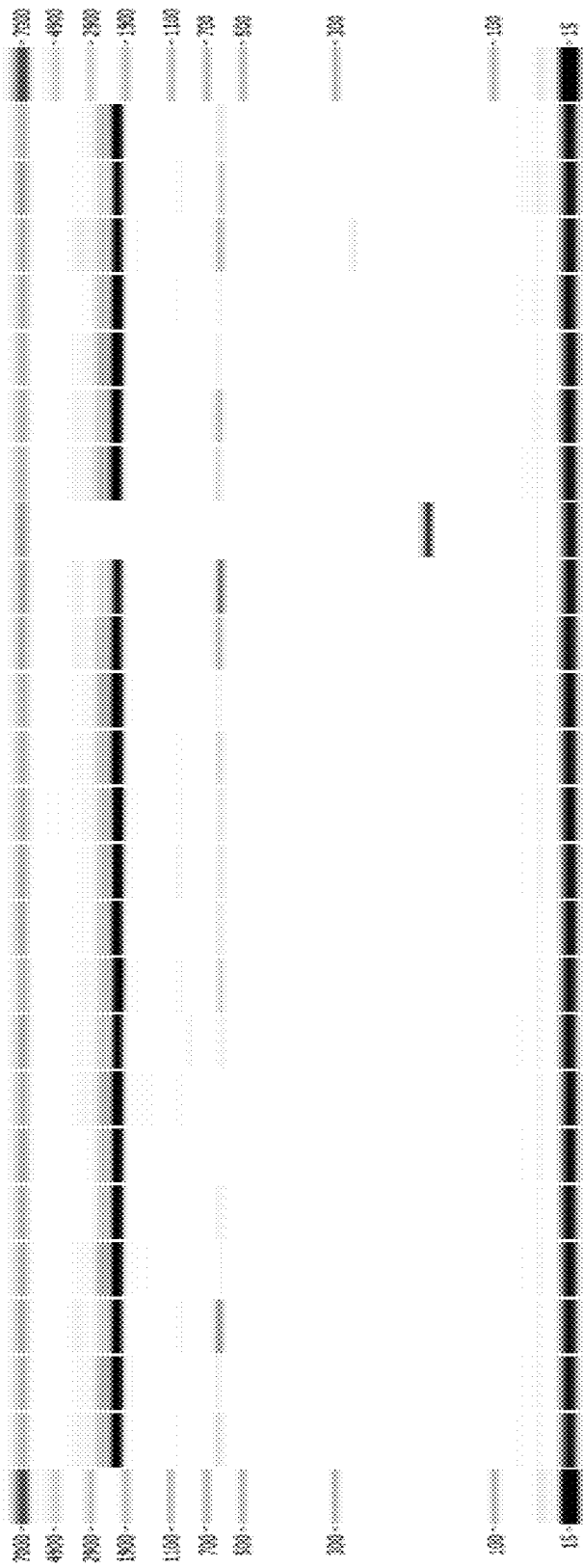
FIG. 2B shows the results from the PCR screen of randomly picked colonies, showing the majority of clones contain the expected full-length insert for exemplary Lab-Chip GX electropherogram results from the 5 fragments plus vector assembly reaction.

The robustness of the assembly reactions carried out in the presence of the chaperone agent Glycerol was demonstrated by screening the resultant colonies from the 10 minute incubation time assemblies by PCR to verify the correct size of assembled fragments. Briefly, colonies were picked and plasmid DNA isolated and added into a PCR reaction containing 0.04 U/µl Immolase DNA Polymerase (Bioline), 1× Immolase buffer, 1.5 mM MgCl$_2$, 0.8 mM dNTPs, and 200 nM each of forward and reverse primer (SEQ ID No 33 and SEQ ID No 34) in a 25 µl PCR reaction with the cycling conditions: 95° C.$^{10:00}$ (95° C.$^{0:10}$-61° C.$^{0:20}$-72° C.$^{0:50}$)×40 cycles+72° C.$^{5:00}$). Table 4 lists the expected sizes of the assembled fragments and the PCR screen primers add an additional 201 bp of pUCIDT AMP vector sequence onto the PCR screen amplicon. The PCR products were analyzed on the LabChip GX (Perkin Elmer). The LabChip GX electropherogram results of the PCR screen for the 4 or 5 fragment plus plasmid, 10 minute assemblies, done in the presence of 6% Glycerol are shown in FIGS. 2A and 2B. The 4 fragment assembly yielded the correct size 1868 bp product 91.7% of the time (22/24 colonies screened) and the 5 fragment assembly yielded the correct size 2261 bp product 95.8% of the time (23/24).

While the rapid incubation time yields full-length assemblies, it is possible that the fragments when joined have errors in the overlap junctions. The fidelity of the assembly reaction under the shortened time was confirmed by sequencing clones picked randomly for the 4 fragment plus plasmid assembly (Table 6). Fully 87% of the clone sequences showed no errors in the assembly reaction as judged by Sanger sequencing over the fragment junctions.

TABLE 1

Sequences used in Example 1

| Seq ID | Sequence |
|---|---|
| SEQ ID No 1 | ATCAGTTCTGGACCAGCGAGCTGT |
| SEQ ID No 2 | ATCTGTCGCCCGTCTCAAACGCA |
| SEQ ID No 3 | GGAGGGTTGCGTTTGAGACGGGCGACAGATCCATGGGAATGGAGGGTATGCTGAAAGGC |
| SEQ ID No 4 | TAGCTGCCAGATAATTGGCTTCACGAGGC |
| SEQ ID No 5 | CGCAGCACAGCTCGCTGGTCCAGAACTGATTAGCTGCCAGATAATTGGCTTCACGAGGC |
| SEQ ID No 6 | TGCCTCGTGAAGCCAATTATCTGGCAG |
| SEQ ID No 7 | CAGCGTATCTTGGCCGCGAAGCG |
| SEQ ID No 8 | CGCAGCACAGCTCGCTGGTCCAGAACTGATCAGCGTATCTTGGCCGCGAAGCG |
| SEQ ID No 9 | GGAGGGTTGCGTTTGAGACGGGCGACAGATGAAGGGTACGACCCGGACCTGGAT |
| SEQ ID No 10 | TTCGAACCGCTTCGCGGCCAAGATACGCTGGAAGGGTACGACCCGGACCTGGAT |
| SEQ ID No 11 | AACGTGGACGAACATAGCCGTAGCGC |
| SEQ ID No 12 | CGCAGCACAGCTCGCTGGTCCAGAACTGATAACGTGGACGAACATAGCCGTAGCGC |
| SEQ ID No 13 | CCGTGCGCTACGGCTATGTTCGTC |
| SEQ ID No 14 | TTCCGCCACTGCGGTGGCAAT |
| SEQ ID No 15 | CGCAGCACAGCTCGCTGGTCCAGAACTGATTTCCGCCACTGCGGTGGCAAT |

TABLE 1-continued

Sequences used in Example 1

| Seq ID | Sequence |
|---|---|
| SEQ ID No 16 | GGTGTAGCGATTGCCACCGCAGT |
| SEQ ID No 17 | CGCAGCACAGCTCGCTGGTCCAGAACTGATCTCGAGGCCTTT<br>CATTGTGTCCAGCG |
| SEQ ID No 18 | ACACTGTTACAGGAATCTTTGCTG |
| SEQ ID No 19 | CTTCCAGCTCCAAGAAATACGC |
| SEQ ID No 20 | CGATCCGGGAGCCTTTATGC |
| SEQ ID No 21 | CAGGTCGTTTGGCACAAACTC |
| SEQ ID No 22 | TAAAACGACGGCCAGT |
| SEQ ID No 23 | CAGGAAACAGCTATGAC |
| SEQ ID No 24 | GGAGGGTTGCGTTTGAGACGGGCGACAGATCCATGGGAATG<br>GAGGGTATGCTGAAAGGCGAAGGACCTGGTCCTCTCCCACCG<br>CTGTTACAACAGTATGTCGAACTTCGTGATCAATACCCAGAT<br>TATCTGCTTTTATTCCAGGTCGGCGATTTTTACGAATGCTTCG<br>GTGAGGATGCAGAGCGCCTGGCCCGTGCCCTTGGCCTGGTAC<br>TGACCCACAAGACGTCCAAAGACTTTACAACGCCTATGGCTG<br>GCATCCCCTCCGTGCGTTTGAAGCTTACGCCGAGCGCTTATT<br>GAAAATGGGCTTTCGTTTGGCCGTCGCTGACCAAGTGGAACC<br>CGCGGAGGAAGCAGAAGGTCTGGTCCGCCGTGAGGTGACCC<br>AACTCCTGACGCCGGGCACACTGTTACAGGAATCTTTGCTGC<br>CTCGTGAAGCCAATTATCTGGCAGCTAATCAGTTCTGGACCA<br>GCGAGCTGTGCTGCG |
| SEQ ID No 25 | GGAGGGTTGCGTTTGAGACGGGCGACAGATCCATGGGAATG<br>GAGGGTATGCTGAAAGGCGAAGGACCTGGTCCTCTCCCACCG<br>CTGTTACAACAGTATGTCGAACTTCGTGATCAATACCCAGAT<br>TATCTGCTTTTATTCCAGGTCGGCGATTTTTACGAATGCTTCG<br>GTGAGGATGCAGAGCGCCTGGCCCGTGCCCTTGGCCTGGTAC<br>TGACCCACAAGACGTCCAAAGACTTTACAACGCCTATGGCTG<br>GCATCCCCTCCGTGCGTTTGAAGCTTACGCCGAGCGCTTATT<br>GAAAATGGGCTTTCGTTTGGCCGTCGCTGACCAAGTGGAACC<br>CGCGGAGGAAGCAGAAGGTCTGGTCCGCCGTGAGGTGACCC<br>AACTCCTGACGCCGGGCACACTGTTACAGGAATCTTTGCTGC<br>CTCGTGAAGCCAATTATCTGGCAGCTA |
| SEQ ID No 26 | TGCCTCGTGAAGCCAATTATCTGGCAGCTATCGCGACGGGCG<br>ACGGCTGGGGACTTGCGTTTTTAGACGTGTCTACCGGCGAAT<br>TTAAGGGTACCGTGCTTAAGAGCAAATCAGCTCTGTACGACG<br>AATTGTTCCGTCATCGCCCTGCTGAAGTTCTGTTAGCCCCCGA<br>GCTGCTCGAAAATGGTGCTTTCCTCGACGAATTCCGCAAACG<br>CTTTTCCGGTGATGCTGTCCGAAGCCCGTTTGAGCCGGAAGG<br>TGAGGGTCCGCTGGCCCTGCGCCGTGCGCGCGGTGCACTGCT<br>GGCCTATGCGCAACGTACGCAGGGCGGTGCTCTGAGCTTGCA<br>GCCGTTTCGTTTCTACGATCCGGGAGCCTTTATGCGCCTGCCG<br>GAAGCTACGTTACGTGCCTTGGAAGTGTTCGAACCGCTTCGC<br>GGCCAAGATACGCTG |
| SEQ ID No 27 | TGCCTCGTGAAGCCAATTATCTGGCAGCTATCGCGACGGGCG<br>ACGGCTGGGGACTTGCGTTTTTAGACGTGTCTACCGGCGAAT<br>TTAAGGGTACCGTGCTTAAGAGCAAATCAGCTCTGTACGACG<br>AATTGTTCCGTCATCGCCCTGCTGAAGTTCTGTTAGCCCCCGA<br>GCTGCTCGAAAATGGTGCTTTCCTCGACGAATTCCGCAAACG<br>CTTTTCCGGTGATGCTGTCCGAAGCCCGTTTGAGCCGGAAGG<br>TGAGGGTCCGCTGGCCCTGCGCCGTGCGCGCGGTGCACTGCT<br>GGCCTATGCGCAACGTACGCAGGGCGGTGCTCTGAGCTTGCA<br>GCCGTTTCGTTTCTACGATCCGGGAGCCTTTATGCGCCTGCCG<br>GAAGCTACGTTACGTGCCTTGGAAGTGTTCGAACCGCTTCGC<br>GGCCAAGATACGCTGATCAGTTCTGGACCAGCGAGCTGTGCT<br>GCG |
| SEQ ID No 28 | GGAGGGTTGCGTTTGAGACGGGCGACAGATTTCGAACCGCTT<br>CGCGGCCAAGATACGCTGGAAGGGTACGACCCGGACCTGGA<br>TGCCTTGCGCGCCGCCCATCGTGAGGGCGTCGCGTATTTCTT<br>GGAGCTGGAAGAGCGCGAGCGTGAACGCACGGGTATCCCCA<br>CGCTGAAAGTAGGCTATAACGCTGTCTTTGGCTACTACCTCG<br>AAGTAACCCGCCCCTACTATGAACGCGTCCCAAAAGAATATC<br>GTCCAGTTCAGACCCTGAAAGATCGTCAGCGCTACACCCTCC<br>CGGAAATGAAAGAGAAGGAACGTGAAGTCTATCGTCTGGAG<br>GCGTTAATTCGTCGCCGGGAGGAAGAGGTGTTTCTTGAAGTT<br>CGTGAGCGGGCCAAACGCCAAGCCGAAGCACTGCGCGAAGC<br>TGCACGTATTCTGGCCGAACTCGATGTCTACGCCGCTCTGGC<br>GGAAGTTGCCGTGCGCTACGGCTATGTTCGTCCACGTT |
| SEQ ID No 29 | TTCGAACCGCTTCGCGGCCAAGATACGCTGGAAGGGTACGAC<br>CCGGACCTGGATGCCTTGCGCGCCGCCCATCGTGAGGGCGTC<br>GCGTATTTCTTGGAGCTGGAAGAGCGCGAGCGTGAAC<br>GGGTATCCCCACGCTGAAAGTAGGCTATAACGCTGTCTTTGG<br>CTACTACCTCGAAGTAACCCGCCCCTACTATGAACGCGTCCC<br>AAAAGAATATCGTCCAGTTCAGACCCTGAAAGATCGTCAGCG<br>CTACACCCTCCCGGAAATGAAAGAGAAGGAACGTGAAGTCT<br>ATCGTCTGGAGGCGTTAATTCGTCGCCGGGAGGAAGAGGTGT<br>TTCTTGAAGTTCGTGAGCGGGCCAAACGCCAAGCCGAAGCAC<br>TGCGCGAAGCTGCACGTATTCTGGCCGAACTCGATGTCTACG<br>CCGCTCTGGCGGAAGTTGCCGTGCGCTACGGCTATGTTCGTC<br>CACGTT |
| SEQ ID No 30 | CCGTGCGCTACGGCTATGTTCGTCCACGTTTCGGCGACCGTCT<br>GCAGATCCGCGCGGGACGTCACCCAGTGGTTGAGCGTCGCAC<br>CGAGTTTGTGCCAAACGACCTGGAAATGGCGCACGAGCTTGT<br>GCTCATCACAGGGCCGAACATGGCTGGCAAAAGCACTTTCCT<br>GCGCCAGACCGCCCTGATTGCACTGTTAGCCCAAGTAGGCAG<br>TTTCGTGCCGGCCGAAGAGGCGCACCTGCCTTTATTCGACGG<br>GATCTATACCCGTATCGGTGCTAGTGACGATCTGGCGGGAGG<br>TAAAAGTACTTTCATGGTGGAAATGAGGAAGTTGCGCTGAT<br>TTTGAAAGAAGCAACGGAGAATAGTCTGGTGTTGCTTGATGA<br>GGTGGGGCGCGGTACAAGTAGTTTAGATGGTGTAGCGATTGC<br>CACCGCAGTGGCGGAA |
| SEQ ID No 31 | CCGTGCGCTACGGCTATGTTCGTCCACGTTTCGGCGACCGTCT<br>GCAGATCCGCGCGGGACGTCACCCAGTGGTTGAGCGTCGCAC<br>CGAGTTTGTGCCAAACGACCTGGAAATGGCGCACGAGCTTGT<br>GCTCATCACAGGGCCGAACATGGCTGGCAAAAGCACTTTCCT<br>GCGCCAGACCGCCCTGATTGCACTGTTAGCCCAAGTAGGCAG<br>TTTCGTGCCGGCCGAAGAGGCGCACCTGCCTTTATTCGACGG<br>GATCTATACCCGTATCGGTGCTAGTGACGATCTGGCGGGAGG<br>TAAAAGTACTTTCATGGTGGAAATGAGGAAGTTGCGCTGAT<br>TTTGAAAGAAGCAACGGAGAATAGTCTGGTGTTGCTTGATGA<br>GGTGGGGCGCGGTACAAGTAGTTTAGATGGTGTAGCGATTGC<br>CACCGCAGTGGCGGAAATCAGTTCTGGACCAGCGAGCTGTGC<br>TGCG |
| SEQ ID No 32 | GGTGTAGCGATTGCCACCGCAGTGGCGGAAGCCCTTCACGAA<br>CGTCGCGCATATACCTTATTTGCGACCCACTATTTTGAACTTA<br>CTGCGTTGGGTCTTCCGCGCCTGAAAAATCTGCACGTAGCCG<br>CTCGCGAAGAAGCGGGTTGGACTGGTCTTTTTATCATCAAGTGC<br>TGCCGGGCCCGGCGAGTAAAAGTTACGGCGTTGAGGTAGCG<br>GCaATGCAGGGCTGCCTAAAGAAGTCGTGGCTCGTGCCCGC<br>GCCTTGCTTCAGGCAATGGCCGCTCGCCGTGAAGGTGCATTG<br>GATGCAGTGTTAGAACGTCTGTTAGCACTTGATCCTGACCGC<br>TTGACCCCGCTTGAAGCGTTACGTCTGCTTCAGGAGCTGAAA<br>GCTCTGGCGTTGGGAGCCCCGCTGGACACAATGAAAGGCCTC<br>GAGATCAGTTCTGGACCAGCGAGCTGTGCTGCG |
| SEQ ID No 33 | GATTAAGTTGGGTAACGCCAGG |
| SEQ ID No 34 | CTATGACCATGATTACGCCACGAG |

TABLE 2

Primer pair combinations used in Example 1.

| Forward Primer | Reverse Primer | Fragment | Fragment size (bp) |
|---|---|---|---|
| 1F-pUCIDT (SEQ ID 3) | 1R (SEQ ID 4) | Fragment V1V (SEQ ID 24) | 477 |
| 1F-pUCIDT (SEQ ID 3) | 1R-pUCIDT (SEQ ID 5) | Fragment V1 (SEQ ID 25) | 447 |
| 2F (SEQ ID 6) | 2R (SEQ ID 7) | Fragment 2 (SEQ ID 26) | 437 |
| 2F (SEQ ID 6) | 2R-pUCIDT (SEQ ID 8) | Fragment 2V (SEQ ID 27) | 467 |
| 3F-pUCIDT (SEQ ID 9) | 3R (SEQ ID 11) | Fragment V3 (SEQ ID 28) | 466 |
| 3-2F (SEQ ID 10) | 3R (SEQ ID 11) | Fragment 3 (SEQ ID 29) | 466 |
| 4F (SEQ ID 13) | 4R (SEQ ID 14) | Fragment 4 (SEQ ID 30) | 437 |
| 4F (SEQ ID 13) | 4R-pUCIDT (SEQ ID 15) | Fragment 4V (SEQ ID 31) | 467 |
| 5F (SEQ ID 16) | 5R-pUCIDT (SEQ ID 17) | Fragment 5V (SEQ ID 32) | 453 |

TABLE 3

Composition of assembly mix

| Component | Final Concentration In Reaction |
|---|---|
| T5 exonuclease (Epicentre) | 0.004 U/ul |
| Phusion DNA polymerase (NEB) | 0.025 U/ul |
| Taq DNA Ligase (Enzymatics) | 0.27 U/ul |
| Tris-HCl pH 7.5 | 100 mM |
| $MgCl_2$ | 10 mM |
| dNTPs, 25 mM each | 0.2 mM each |
| DTT | 10 mM |
| NAD | 1 mM |
| PEG-8000 or Glycerol | 5 or 6% w/v |

TABLE 4

Fragments combined for assembly reactions and expected insert size(s)

| Number of Fragments | Fragment | Expected insert size (bp) |
|---|---|---|
| 1 | V1V (SEQ ID 24) | 417 |
| 2 | V1 (SEQ ID 25) 2V (SEQ ID 27) | 824 |
| 3 | V3 (SEQ ID 28) 4 (SEQ ID 30) 5V (SEQ ID 32) | 1236 |
| 4 | V1 (SEQ ID 25) 2 (SEQ ID 26) 3 (SEQ ID 29) 4V (SEQ ID 31) | 1667 |
| 5 | V1 (SEQ ID 25) 2 (SEQ ID 26) 3 (SEQ ID 29) 4 (SEQ ID 30) 5V (SEQ ID 32) | 2060 |

TABLE 5

Colony count results as a function of incubation time and the number of fragments used in assembly reaction.

| Incubation time | Isothermal Mix Formulation | 1 | 2 | 3 | 4 | 5 | Vector only |
|---|---|---|---|---|---|---|---|
| 60 min | 5% PEG-8000 | >2000 | >1000 | 812 | 704 | 460 | 1 |
| 60 min | 6% Glycerol | >2000 | >1000 | 944 | 588 | 496 | 1 |
| 10 min | 5% PEG-8000 | >1000 | 812 | 768 | 46 | 106 | 1 |
| 10 min | 6% Glycerol | >2000 | >1000 | 856 | 840 | 856 | 12 |
| 5 min | 5% PEG-8000 | 384 | 80 | 30 | 5 | 1 | 2 |
| 5 min | 6% Glycerol | >2000 | >1000 | 384 | 256 | 45 | 16 |

TABLE 6

Sanger sequencing results for 4 fragment assembly

| Incubation Time | Isothermal Mix Formulation | Percent of clones with correctly assembled sequence |
|---|---|---|
| 60 min | 5% PEG-8000 | 66% (12/18) |
| 60 min | 6% Glycerol | 100% (16/16) |
| 10 min | 6% Glycerol | 87% (20/23) |

Figure 3:
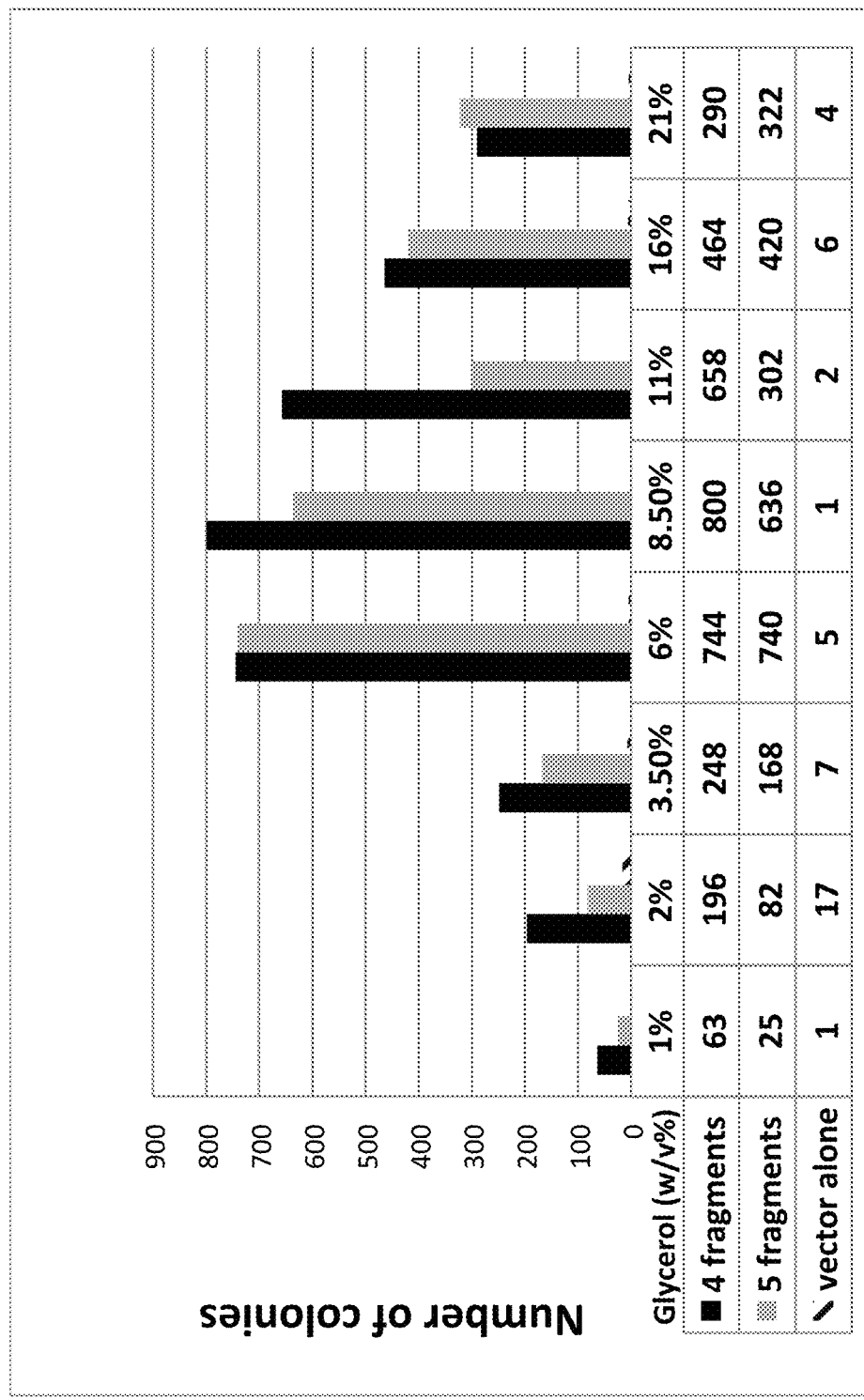
FIG. 3 shows the colony counts obtained when the isothermal assembly mix contains an increasing amount of the chaperone agent Glycerol.
Figure 4A:
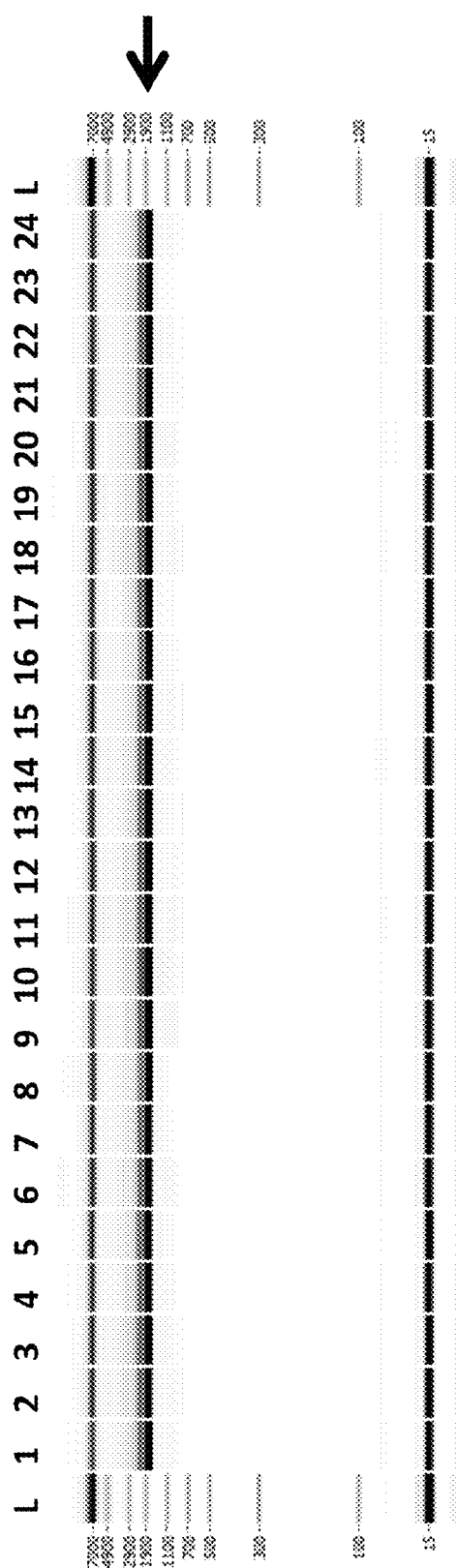
FIG. 4A shows the results the PCR screen of randomly picked colonies, showing the majority of clones contain the expected full length insert when the isothermal assembly mix contains 8.5% Glycerol for exemplary LabChip GX electropherogram results from the 4 fragment plus vector assembly reaction.
Figure 4B:
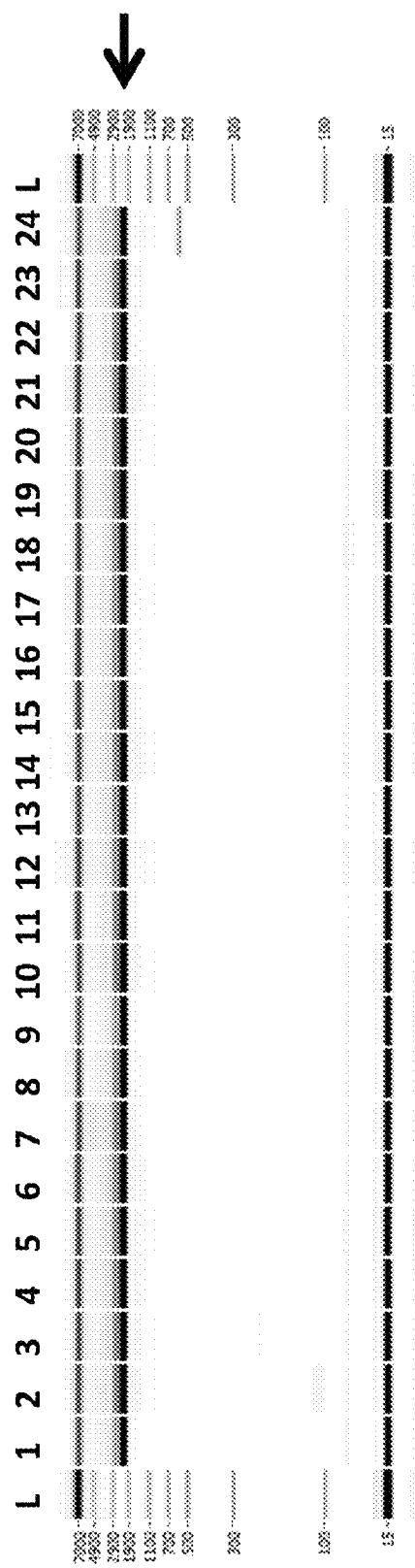
FIG. 4B shows the results the PCR screen of randomly picked colonies, showing the majority of clones contain the expected full length insert when the isothermal assembly mix contains 8.5% Glycerol for exemplary LabChip GX electropherogram results from the 5 fragment plus vector assembly reaction.

Example 2: Determination of the Optimal Concentration of the Chaperone Agent Glycerol Since the isothermal assembly mix contains three different enzymes, each of which comes from the manufacturer with glycerol already added, upon creating the mixture of enzymes and other components, there is a minimal amount of glycerol present (1%). To determine the optimal concentration, a range of Glycerol percentages were tested 1-21% (w/v), with either 4 or 5 fragments with 30 bp overlapping sequences, and a linearized plasmid vector. The fragments and vector were incubated in the assembly mix for 10 minutes at 50° C. One microliter of the assembled material was transformed into 30 uL of XL-1 Blue supercompetent bacteria, heat shocked at 42° C. for 30 seconds, 200 uL of LB was added and cells were allowed to recover at 37° C. 50 uL of the transformation mixture was plated on the agar plates containing the appropriate antibiotic (ampicillin, 100 ug/mL). Control reactions consisted of incubating only vector DNA in the presence of the assembly mix. FIG. 3 shows the optimal percentage of glycerol was between 6-8.5%, well above the residual amount that is coming from the enzymes. The optimal glycerol concentration in the assembly as monitored by PCR screening of randomly chosen colonies was still very robust, wherein 24/24 picked colonies were identified with the full length assembled product (FIG. 4). Furthermore, too much Glycerol was detrimental to the assembly reaction as observed by the lower number of colonies observed.

Figure 5:
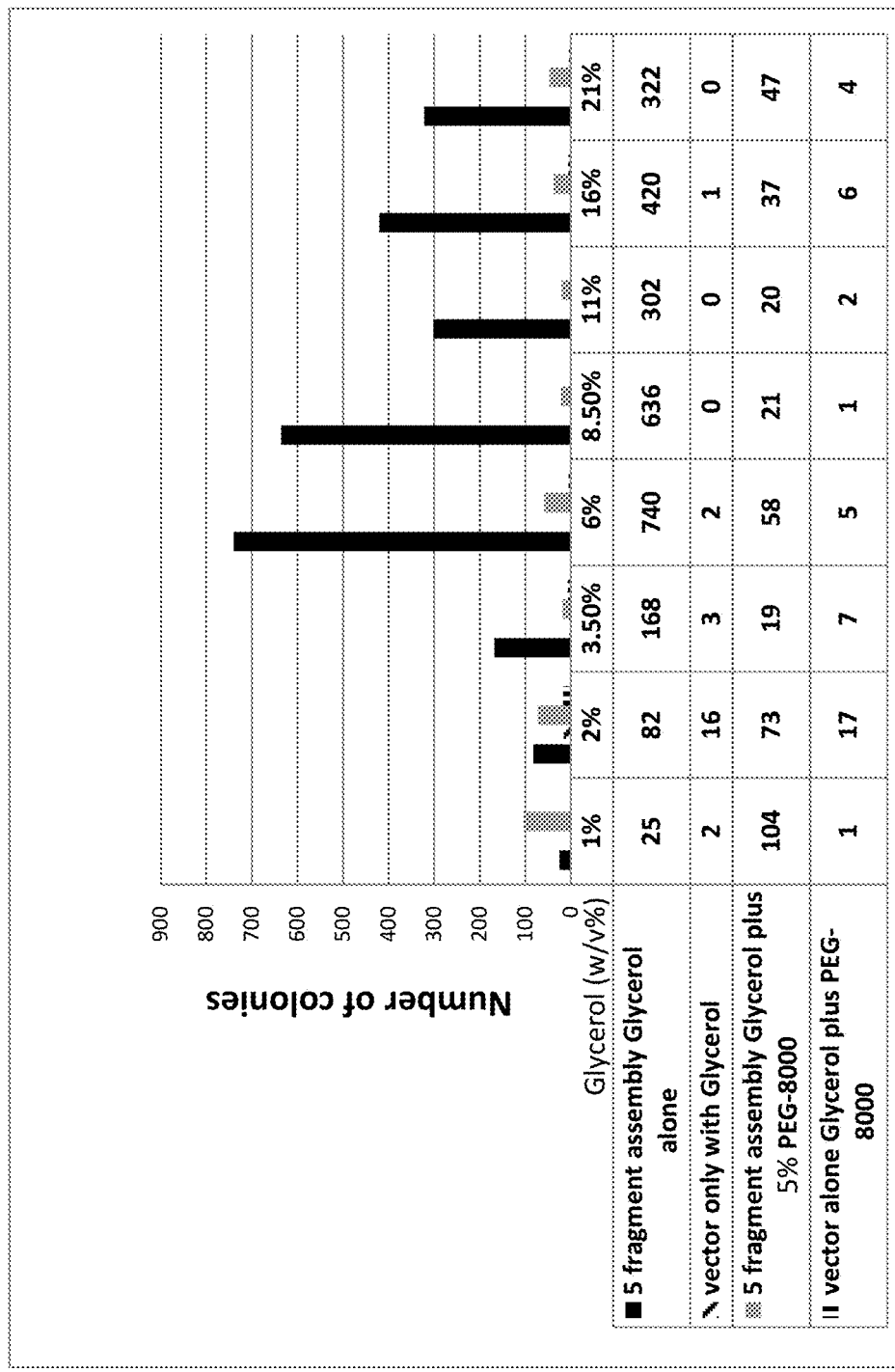
FIG. 5 shows the colony counts obtained when the isothermal assembly reaction is carried out in the presence of both crowding agent PEG-8000 and chaperone agent Glycerol using 5 fragments plus vector. The counts for Glycerol alone are indicated by the solid black bars, the counts for PEG-8000 and Glycerol are indicated by grey bars, the vector alone in Glycerol control is indicated by the vertical hatch bars, and the vector alone with PEG-8000 and Glycerol are slanted cross hatched.

Example 3: Crowding Agents in the Presence of Chaperone Agents Negatively Impact the Assembly Process To determine if the addition of both crowding agents and chaperone agents are compatible, the same assembly reactions as shown in FIG. 3 were carried out in the presence of 5% PEG8000 and varied amounts of glycerol. Assembly was carried out with 5 fragments, each with 30 bp overlapping sequences, and a linearized plasmid vector. The fragments and vector were incubated in the assembly mix for 10 minutes at 50° C. One microliter of the assembled material was transformed into 30 uL of XL-1 Blue supercompetent bacteria, heat shocked at 42° C. for 30 seconds, 200 uL of LB was added and cells were allowed to recover at 37° C. 50 uL of the transformation mixture was plated on the agar plates containing the appropriate antibiotic (ampicillin, 100 ug/mL). The results shown in FIG. 5 clearly indicate that the two reagents are not compatible. The efficiency of the assembly process is greatly inhibited in the presence of PEG8000. At the optimal glycerol concentration of 8.5%, the presence of PEG8000 lowers the number of colonies obtained from the assembly process using 4 fragments from 800 to 19, a greater than forty fold decrease.

Example 4: Other Chaperone Agents have Similar Enhancing Properties

Figure 6:
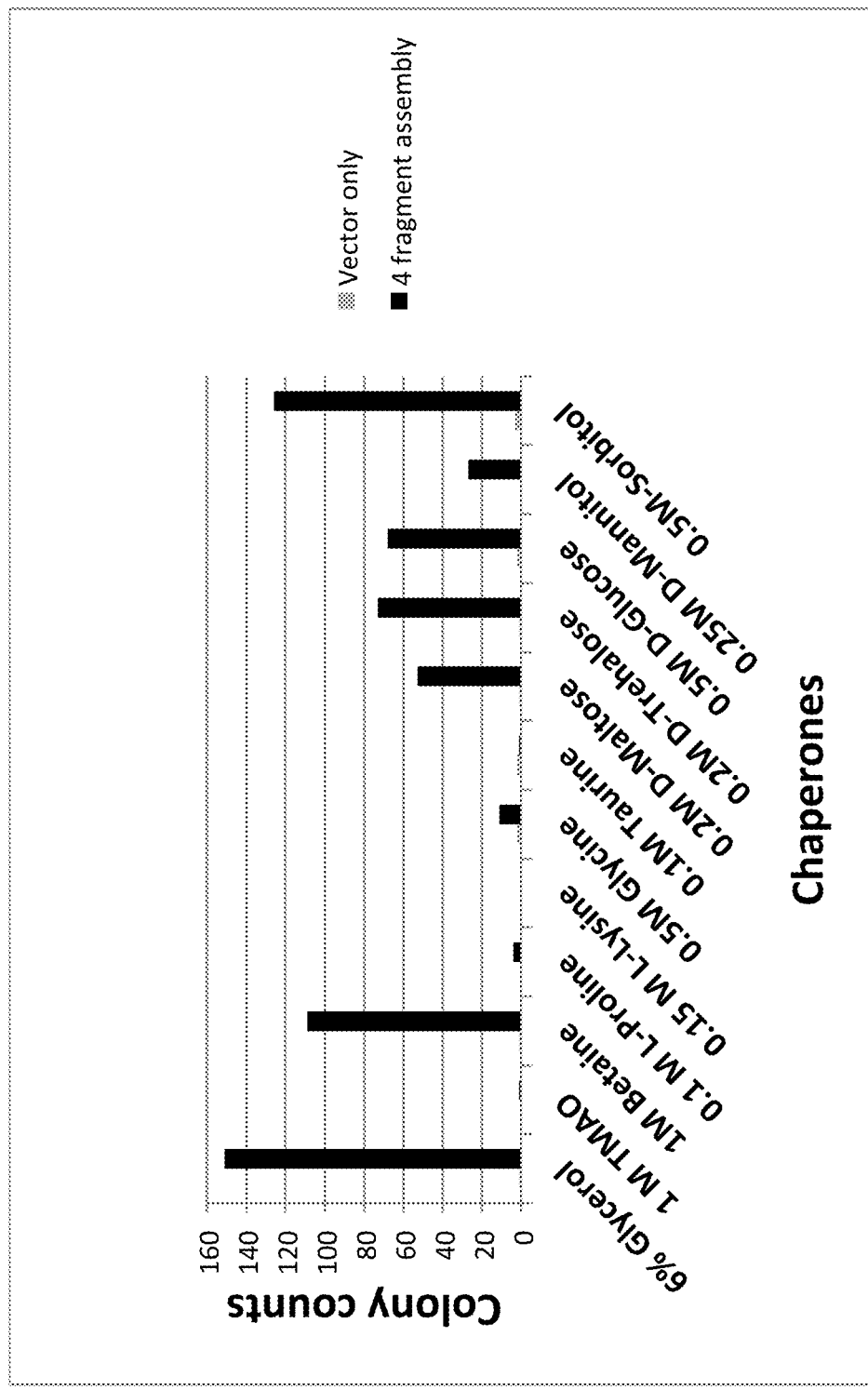
FIG. 6 shows the colony counts obtained when the isothermal assembly reaction is carried out in the presence of various chaperone agents, using 4 fragments plus vector assembly reaction.

The chaperone agent glycerol is a member of a general chemical class knows as sugar alcohols. Additional chaperone agents were tested to see if they too could act in a similar manner as glycerol, and be a substitute for a crowding agent in the assembly mixture. General classes tested included methylamines, sugars as well as sugar alcohols. Four overlapping fragments and plasmid were incubated with the various chaperone mixes at 50° C. for 10 minutes, 1 µL was transformed into 30 µL XL1 Blue supercompetent cells, heat shocked at 42° C. for 45 seconds, 1 mL of SOC was added and cells were allowed to recover at 37° C. 50 uL of the transformation mixture was plated on the agar plates containing the appropriate antibiotic (ampicillin, 100 ug/mL). The methylamine Betaine (2-trimethylammonioacetate), sugars Trehalose ((2R,3S,4S,5R,6R)-2-(Hydroxymethyl)-6-[(2R,3R,4S,5S,6R)-3,4,5-trihydroxy-6-(hydroxymethyl)oxan-2-yl]oxyoxane-3,4,5-triol), Glucose ((2R,3S,4R,5R)-2,3,4,5,6-Pentahydroxyhexanal) and the sugar alcohol Sorbitol ((2S,3R,4R,5R)-Hexane-1,2,3,4,5,6-hexol) were especially effective as crowding agent substitutes, FIG. 6.

Figure 7A:
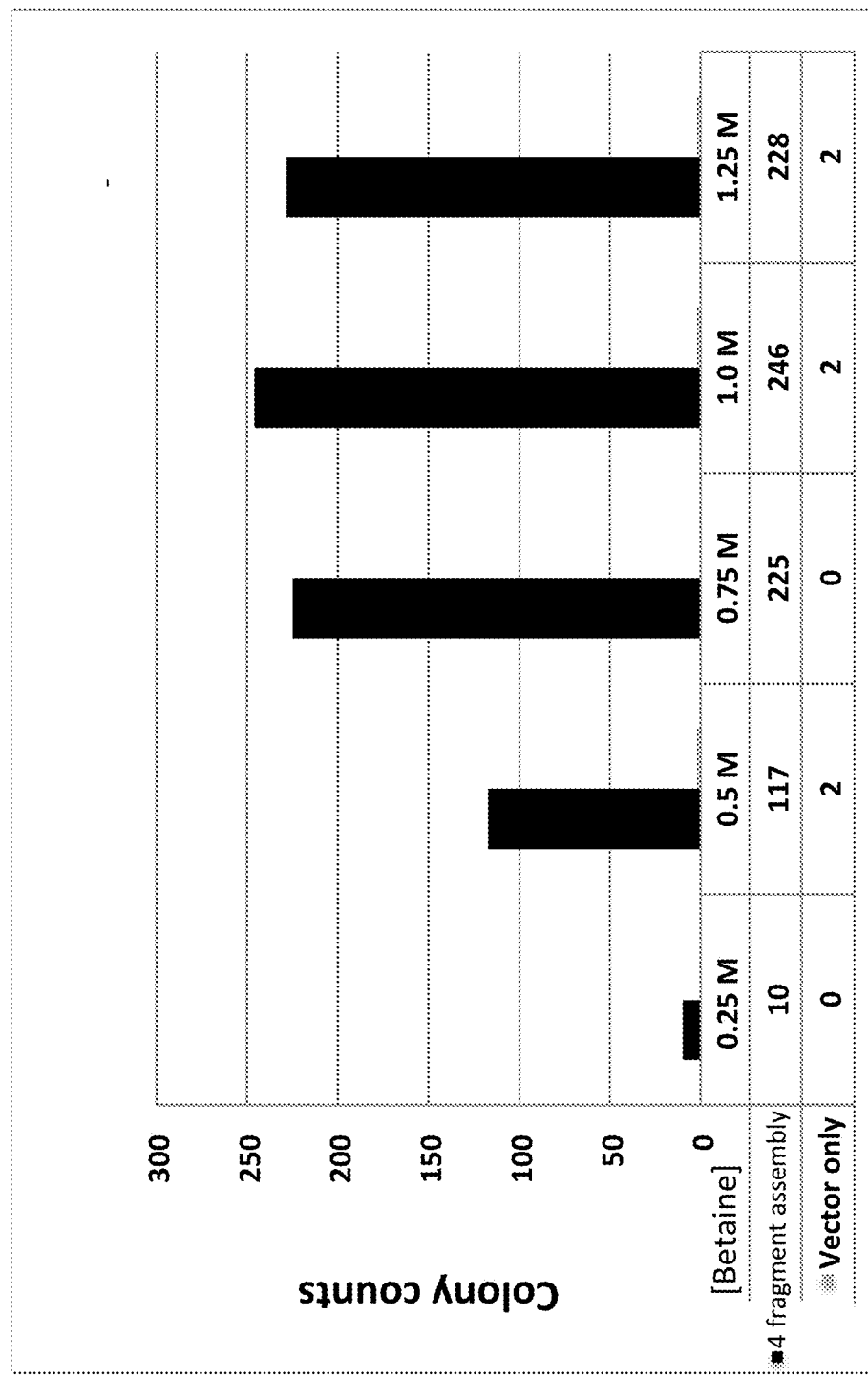
FIG. 7A shows the colony counts obtained when the isothermal assembly reaction is carried out in the presence of different concentrations of Betaine (0.25M to 1.25M) using 4 fragments plus a linear vector.
Figure 7B:
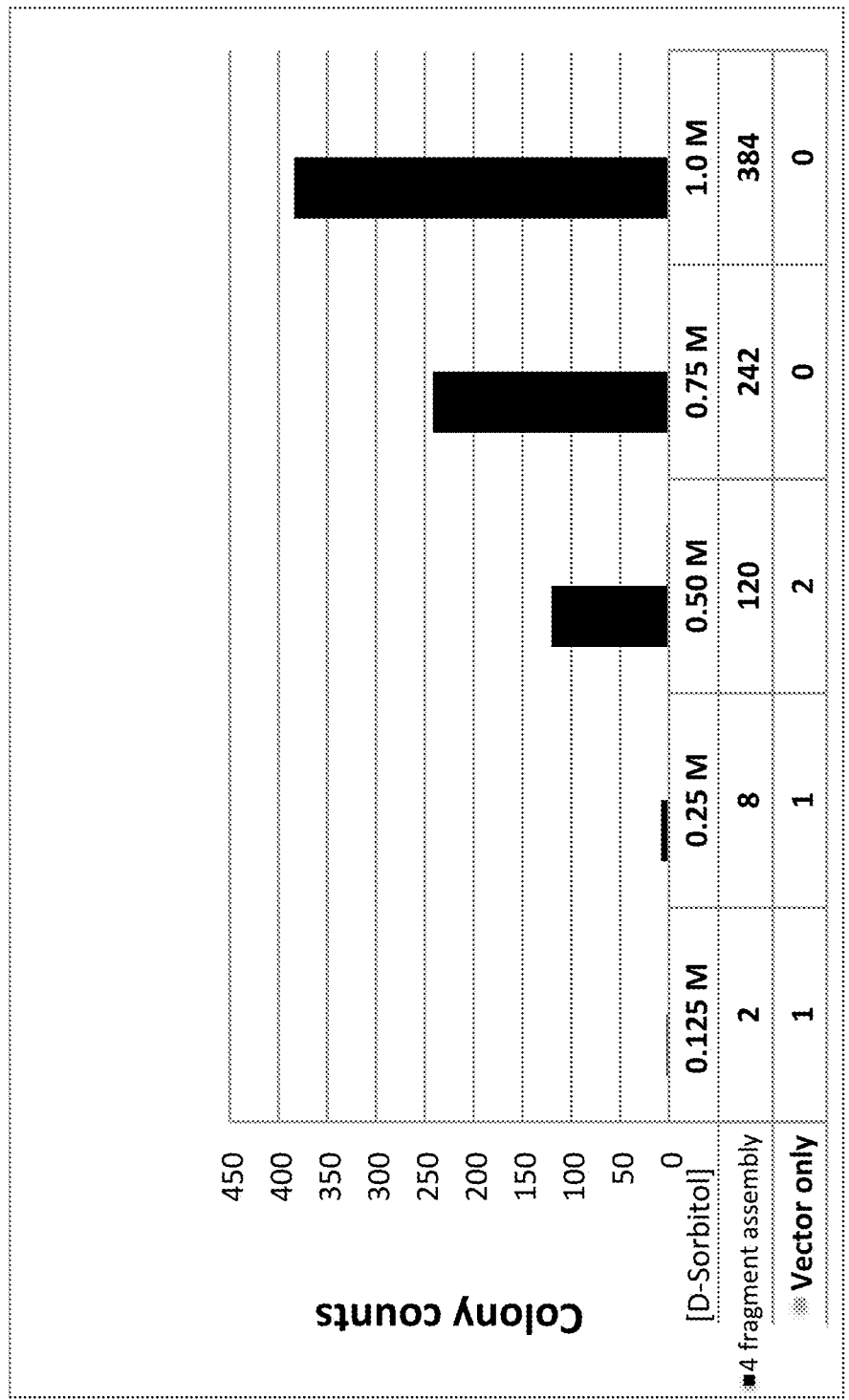
FIG. 7B shows the colony counts obtained when the isothermal assembly reaction is carried out in the presence of different concentrations of D-Sorbitol (0.125 M to 1.0 M) using 4 fragments plus a linear vector.
Figure 7C:
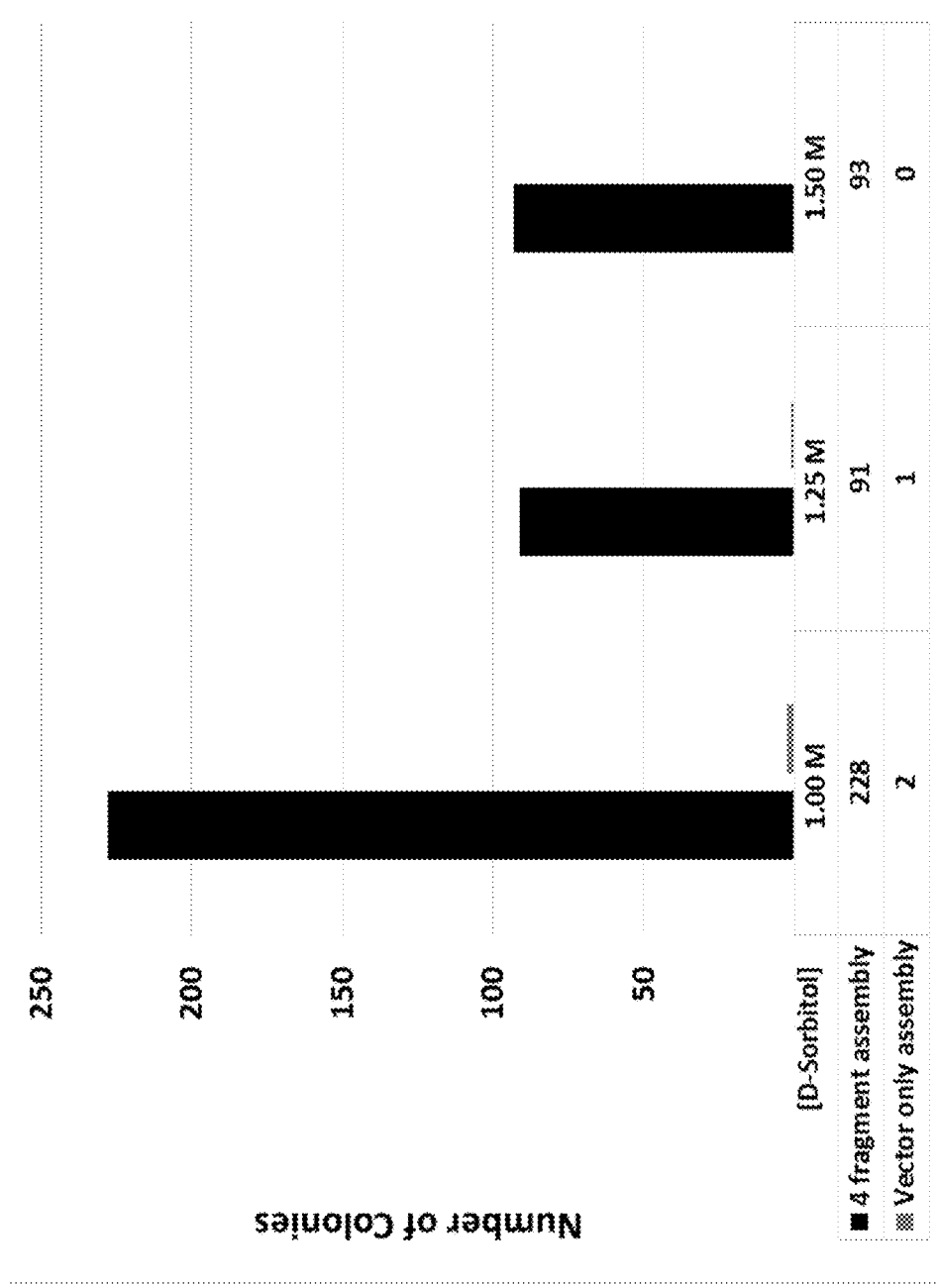
FIG. 7C shows the colony counts obtained when the isothermal assembly reaction is carried out in the presence of different concentrations of D-Sorbitol (1.00 M to 1.50 M) using 4 fragments plus a linear vector.

Example 5: Determining Optimal Concentration of the Chaperone Agents Betaine and D-Sorbitol Four fragments with 30 bp overlaps and a linearized plasmid vector were incubated at 50° C. for 10 minutes with assembly mixes containing varying concentrations of Betaine or D-Sorbitol, 1 uL was transformed into 30 µL XL1 Blue supercompetent cells, heat shocked at 42° C. for 45 seconds, 1 mL of SOC was added and cells were allowed to recover at 37° C. for 1 hour. 50 µL of the transformation mixture was plated on the agar plates containing the appropriate antibiotic (ampicillin, 100 ug/mL). Colonies were counted and the results are displayed in FIGS. 7A and 7B. Betaine showed an optimal concentration of 1 M, while the optimal concentration of D-Sorbitol was 1 M. A second titration was carried out using a higher concentration of D-Sorbitol (1.0 M, 1.25 M, 1.5 M) and the results are shown in FIG. 7C. While the number of colonies obtained was maximal at 1 M, the increased concentration still yield a very significant increase in the number of colonies as compared to the vector alone assembly.

Example 6: Chaperone Agents Accelerate the Actual Assembly Process

Figure 8:
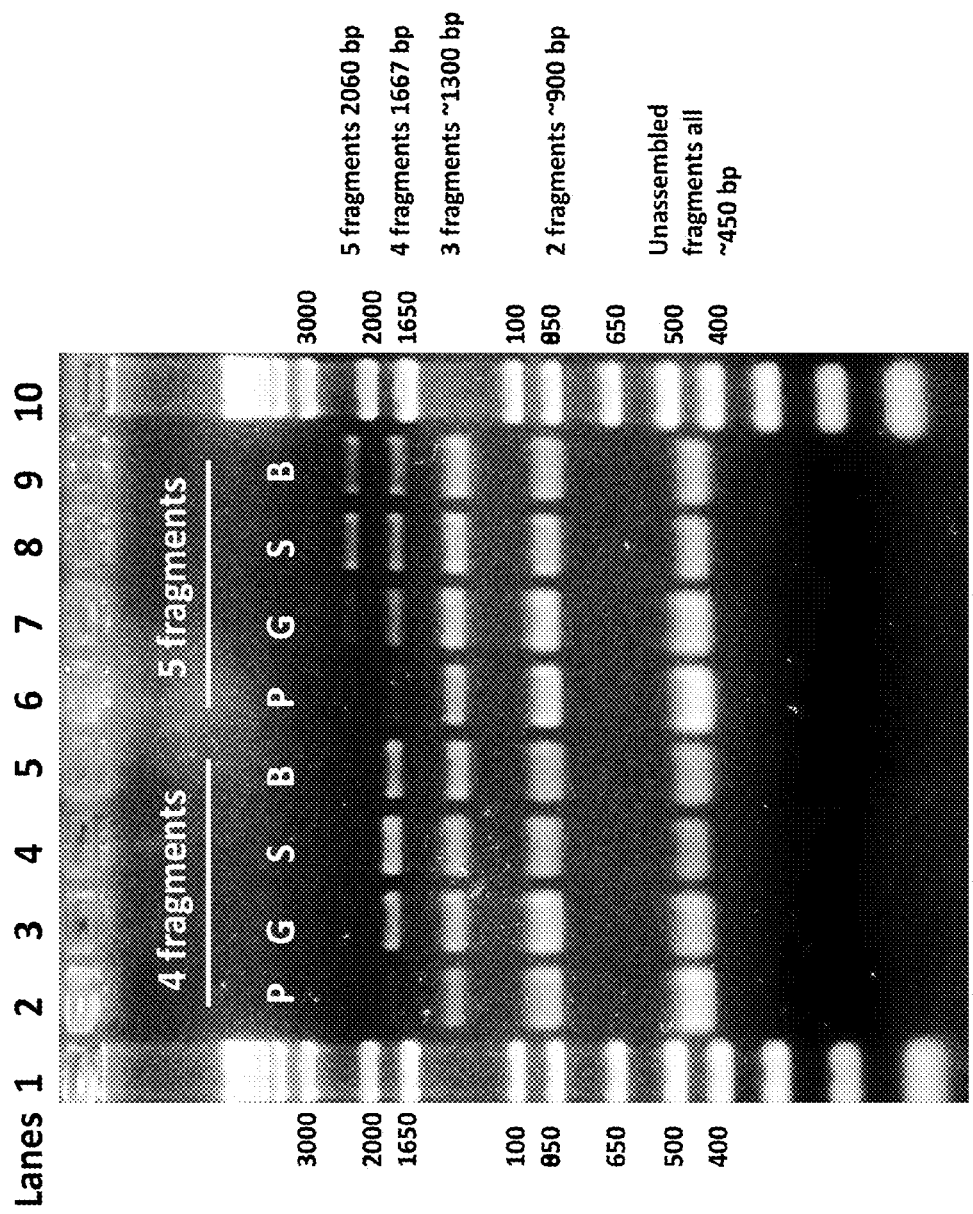
FIG. 8 shows the results of the assembly products run out on a 1% agarose gel generated according to Example 6. Molecular weight markers are seen in lanes 1 and 10. Lanes 2-5 represent the results of the 4 fragment assembly reactions performed in the presence of either PEG-8000 (P), Glycerol (G), Sorbitol (S) or Betaine (B). Lanes 6-9 represent the results when five fragments are used.

Four or five fragments (140 moles each fragment, equal molar amounts) with 30 bp overlaps were incubated at 50° C. for 10 minutes with assembly mixes containing either: 5% PEG-8000, 6% Glycerol, 1 M Betaine or 1M Sorbitol. The DNA was purified from the reaction mix using Agencourt AMPure XP beads (Beckman Coulter) using a bead:DNA volume ratio of 1.8:1 and following the protocol as outlined by the vendor. The samples were run on a 1.5% agarose gel (1×TBE buffer) and stained with GelRed nucleic acid stain (Biotium), and visualized on a UV transilluminator at 305 nm. Lanes 2-5 of FIG. 8 show the four fragment assembly results. Comparison of the band intensities at the 1667 bp position show almost no full length product with the assembly mix containing the crowding agent PEG-8000 (FIG. 8: lane 2, P), and a strong full length product signal observed from the isothermal assemblies done in the presence of Glycerol (FIG. 8: lane 3, G), Sorbitol (FIG. 8: lane 4) and Betaine (FIG. 8: lane 5, B). The five fragment assembly results also show almost no full length product (2060 bp) from the PEG-8000 mix (lane 6, P) and even very tiny amounts of the 4 fragment intermediate assembly (1667 bp), whereas the chaperone agent-containing mixes give robust full length products (FIG. 8: lanes 7-9, G-S-B).

Example 7: Addition of Chaperone Agents in the Assembly Mix does not Alter the Transformation Efficiency of the Competent Bacteria To test whether the mode of action of the chaperones were just enhancing the ability of chemically competent bacteria to uptake plasmid DNA, 6 different assembly mixes were tested. All mixes contain 1% residual glycerol from the component enzymes with or without additional chaperones or PEG-8000. 35 femtomoles of a 6.45 Kb supercoiled plasmid was combined with the mixes and 1 µL of that mixture was transformed into 30 µL of XL1-Blue supercompetent bacteria heat shocked at 42° C. for 45 seconds, 1 mL of SOC was added and cells were allowed to recover at 37° C. for 1 hour. The recovered transformation was diluted 500-fold in SOC and 50 µl was plated onto the appropriate antibiotic containing agar plates. Resulting colony counts are shown in TABLE 7. Treatment with or without the chaperones Glycerol, D-Sorbitol or Betaine showed no enhancement of transformation efficiency over the PEG controls.

TABLE 7

Colony count results of effect of additive on bacterial transformation.

| Additive in 1X Assembly mix | Number of Colonies |
|---|---|
| No additive | 282 |
| 5% PEG | 374 |
| 5% Glycerol | 304 |
| 20% Glycerol | 350 |
| 1M D-Sorbitol | 354 |
| 1M Betaine | 310 |

Example 8: Chaperone Based Enhancement of Assembly is Independent of the Presence of a DNA Ligase Three fragments with 30 bp overlaps and a linearized plasmid vector were incubated at 50° C. for 10 minutes in six different assembly mixes as shown in TABLE 8.

TABLE 8

Assembly mixes with different combinations of additives.

| Assembly Mix | Additive Component(s) in Assembly Mix | | |
|---|---|---|---|
| | T4 DNA Ligase | PEG-8000 (5%) | Sorbitol (1M) |
| 1 | Absent | Absent | Absent |
| 2 | Absent | Present | Absent |
| 3 | Absent | Absent | Present |
| 4 | Present | Absent | Absent |
| 5 | Present | Present | Absent |
| 6 | Present | Absent | Present |

The same reactions were also set up with only the linearized plasmid vector and did not include the fragments. The assembly reactions were transformed into 30 µL XL1 Blue supercompetent cells, heat shocked at 42° C. for 45 seconds, 1 mL of SOC was added and cells were allowed to recover at 37° C. for 1 hour. One hundred microliters (100 µL) of each transformation was plated onto 3 replicate agar plates containing the appropriate antibiotic. The amount of transformation mixture plated was increased over previous examples, resulting in an increase in the overall number of colonies seen in this series of assemblies.

Figure 9:
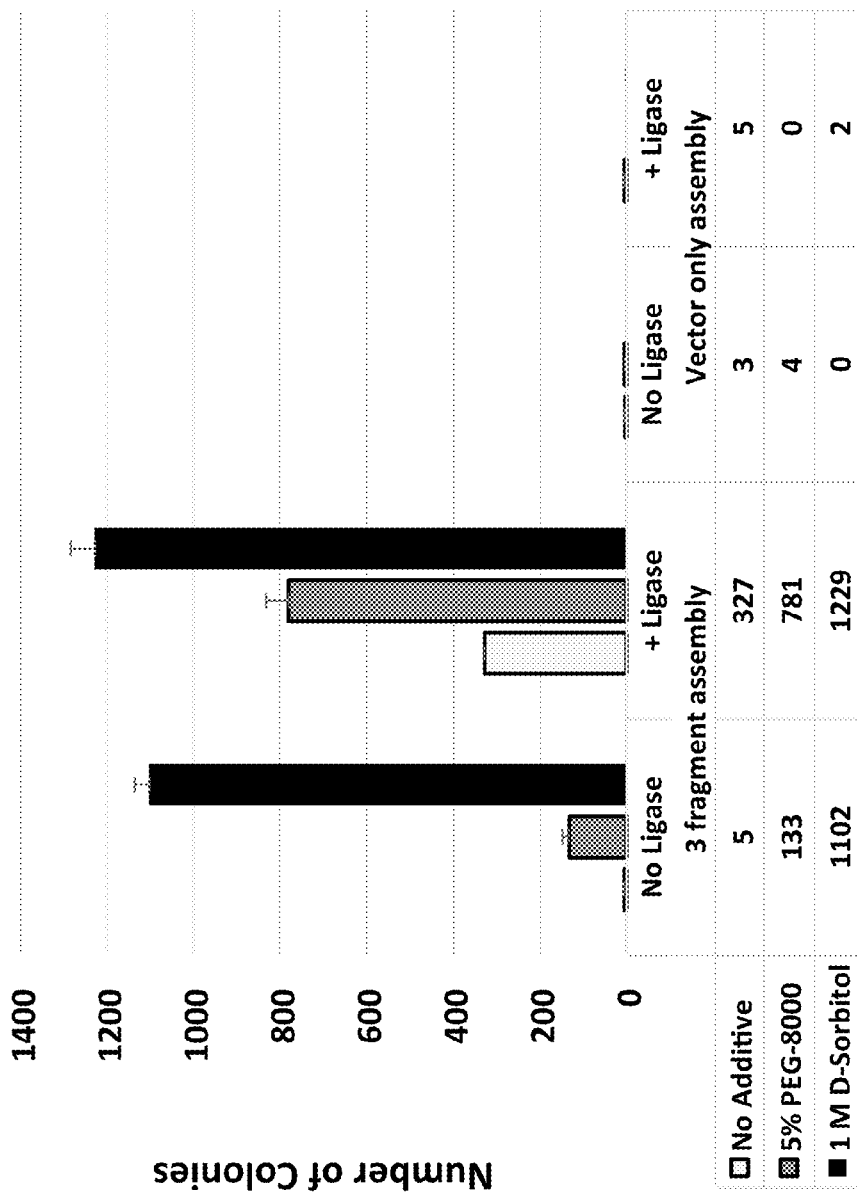
FIG. 9 shows colony count results as a function of different combinations of additives (T4 DNA Ligase, 5% PEG-8000 and 1.0 M D-Sorbitol) in the assembly reaction.

The resultant colony counts are shown in FIG. 9. Error bars indicate standard error. The results clearly show that the presence of a DNA ligase is not an absolute requirement for assembly to occur in vivo. Furthermore, the chaperone D-Sorbitol shows the same increased enhancement of assembly over PEG as seen in the other examples. In the absence of fragments, the vector alone controls show no significant number of colonies, showing that the assembly process is dependent on the overlapping fragments.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences that reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

The terminology used herein is for the purpose of describing particular embodiments only, and is not intended to be limiting. With respect to the use of substantially, any plural and/or singular terms herein, those having skill in the art can translate from the plural as is appropriate to the context and/or application. The various singular/plural permutations may be expressly set forth herein for the sake of clarity.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiments or examples disclosed, but that the present invention will include all embodiments falling within the scope of the appended claims.

What is claimed is:

1. A composition for joining a first set of double-stranded (ds) DNA molecules, the composition comprises:
   (a) an isolated enzyme that exhibits a 3' or 5' exonuclease activity;
   (b) a non strand-displacing DNA polymerase;
   (c) a DNA ligase that is compatible with the DNA polymerase in (b); and
   (d) a chaperone agent,
   wherein the chaperone agent is selected from the group consisting of glycerol, sorbitol and betaine, wherein if the chaperone agent is glycerol, then a final concentration of glycerol from about 6 to 8.5% w/v is present in a final mixture comprising the first set of double-stranded (ds) DNA molecules and the components of the composition.

2. The composition of claim 1, wherein the isolated enzyme that exhibits a 3' or 5' exonuclease activity comprises T4 DNA polymerase.

3. The composition of claim 1, wherein the non strand-displacing DNA polymerase comprises Taq DNA polymerase.

4. The composition of claim 1, wherein the DNA ligase comprises Taq DNA ligase.

5. The composition of claim 1, wherein the chaperone agent is glycerol.

6. The composition of claim 1, wherein the chaperone agent is sorbitol or betaine.

7. A kit for joining a first set of double-stranded (ds) DNA molecules, the kit comprises:
   (a) an isolated enzyme having a 3 or 5 exonuclease activity;
   (b) an isolated non strand-displacing DNA polymerase;
   (c) an isolated ligase that is compatible with the isolated non strand-displacing polymerase of (b); and
   (d) a reagent solution comprising a chaperone agent,
   wherein the chaperone agent is selected from the group consisting of glycerol, sorbitol and betaine, wherein if the chaperone agent is glycerol, then a final concentration of glycerol from about 6 to 8.5% w/v is present in a final mixture comprising the first set of double-stranded (ds) DNA molecules and the components of the kit.

8. The kit of claim 7, wherein the isolated enzyme that exhibits a 3' or 5' exonuclease activity comprises T4 DNA polymerase.

9. The kit of claim 7, wherein the isolated non strand-displacing DNA polymerase comprises Taq DNA polymerase.

10. The kit of claim 7, wherein the isolated ligase comprises Taq DNA ligase.

11. The kit of claim 7, wherein the chaperone agent is glycerol.

12. The kit of claim 7, wherein the chaperone agent is sorbitol or betaine.

13. The kit of claim 7, wherein the reagent solution comprises a concentrated amount of the chaperone agent sufficient to enhance joining the first set of double-stranded (ds) DNA molecules in a final mixture comprising the first set of double-stranded (ds) DNA molecules and the components of the kit.

14. The kit of claim 13, wherein the concentrated amount of the chaperone agent comprises an amount of sorbitol to provide a final concentration from about 0.25 M to about 1.50 M in the final mixture comprising the first set of double-stranded (ds) DNA molecules and the components of the kit.

15. The kit of claim 13, wherein the reagent solution further comprises a concentrated amount of Tris pH7.5 buffer sufficient to support joining the first set of double-stranded (ds) DNA molecules in a final mixture comprising the first set of double-stranded (ds) DNA molecules and the components of the kit.

16. The kit of claim 7, further comprising instructions.

17. The composition of claim 6, wherein the composition provides a final concentration of sorbitol or betaine at least 0.25M in a final mixture comprising the first set of double-stranded (ds) DNA molecules and the components of the composition.

18. The kit of claim 12, wherein the composition provides a final concentration of sorbitol or betaine at least 0.25M in a final mixture comprising the first set of double-stranded (ds) DNA molecules and the components of the kit present in a composition for joining a first set of double-stranded (ds) DNA molecules.

\* \* \* \* \*